(12) United States Patent
Takahashi et al.

(10) Patent No.: US 6,511,830 B1
(45) Date of Patent: Jan. 28, 2003

(54) KILLER T CELL RECEPTOR RECOGNIZING HUMAN IMMUNODEFICIENCY VIRUS

(75) Inventors: Hidemi Takahashi, 3-49-11, Wada, Suginami-ku, Tokyo 166-0012 (JP); Takashi Saito, 3-6-25, Meiwa, Yotsukaido-shi, Chiba 284-0043 (JP)

(73) Assignees: Kyowa, Hakko Kogyo Co., Ltd. (JP); Hidemi Takahashi (JP); Takashi Saito (JP)

( * ) Notice: Subject to any disclaimer, the term of this patent is extended or adjusted under 35 U.S.C. 154(b) by 0 days.

(21) Appl. No.: 09/509,347

(22) PCT Filed: Sep. 28, 1998

(86) PCT No.: PCT/JP98/04345

§ 371 (c)(1),
(2), (4) Date: Mar. 27, 2000

(87) PCT Pub. No.: WO99/16885

PCT Pub. Date: Apr. 8, 1999

(30) Foreign Application Priority Data

Sep. 26, 1997 (JP) .............................................. 9-262536

(51) Int. Cl.⁷ .......................... G01N 33/53; C12Q 1/70; A61K 39/42; A61K 39/21; C07K 1/00
(52) U.S. Cl. .......................... 435/72; 435/5; 424/208.1; 424/160.1; 530/350
(58) Field of Search ...................... 530/350; 424/208.1, 424/160.1; 435/7.2, 5

(56) References Cited

U.S. PATENT DOCUMENTS 4,873,190 A   10/1989   Saito et al. .............. 435/172.3
5,316,925 A   5/1994    Davis et al. ................ 435/91.2

FOREIGN PATENT DOCUMENTS

| JP | 63276496   | 11/1988 |
| WO | WO 95/16462 | 6/1995 |

OTHER PUBLICATIONS

Yanagi et al., Analysis of cDNA clones specific for human T cells and . . . , Proc. Natl. Acad. Sci. USA, vol. 82 (1985), pp. 3430–3434.

J. Clin. Invest, The American Society for Clinical Investation, Inc., Voll. 86, Dec. 1990, pp. 2117–2124.

*Primary Examiner*—Hankyel T. Park
(74) *Attorney, Agent, or Firm*—Fitzpatrick, Cella, Harper & Scinto

(57) ABSTRACT

The present invention relates to a polypeptide which is a constituent of a killer T cell receptor and is capable of injuring human immunodeficiency virus-infected cells; a DNA encoding this polypeptide; a recombinant vector comprising this DNA and a vector; a transformant obtained by transferring this recombinant vector into a host cell; a process for producing the above polypeptide characterized by culturing the above transformant in a medium, thus forming and accumulating the polypeptide in the culture and then recovering the polypeptide from the culture; an antibody reacting specifically with the above polypeptide; human-mouse type killer T cell receptor αchain and βchain in each of which the variable region site of the above polypeptide is sustained while the constant region site thereof has been replaced by that of the human type; transgenic animals having the above polypeptide expressed therein; and anti-HIV agents containing the above polypeptide.

25 Claims, 16 Drawing Sheets

FIG. 12
TCRα chain
RT-PCR
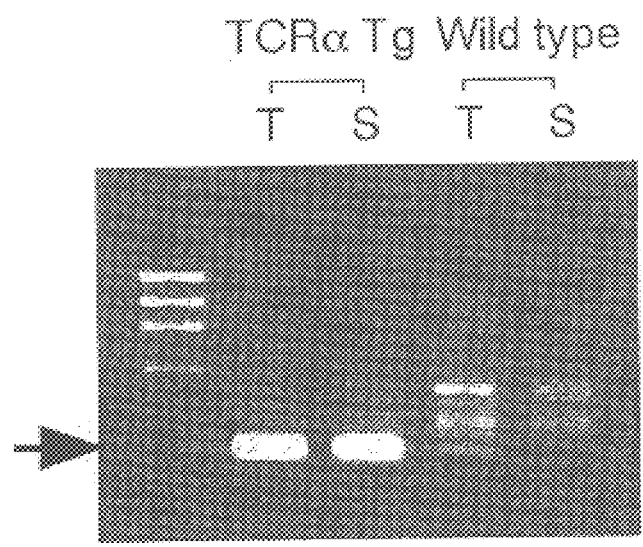
T: Thymus
S: Spleen
TCRβ chain
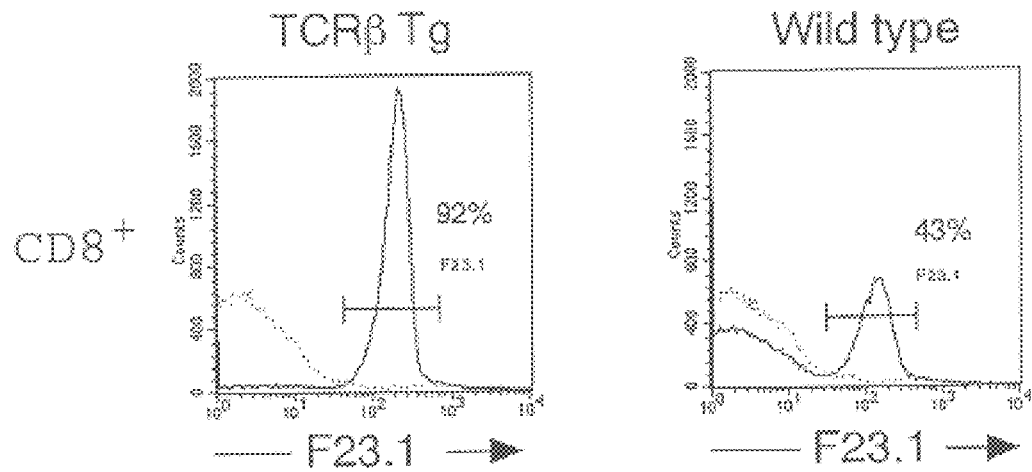

KILLER T CELL RECEPTOR RECOGNIZING HUMAN IMMUNODEFICIENCY VIRUS

TECHNICAL FIELD

The present invention relates to a polypeptide which is a constituent of a killer T cell receptor capable of specifically injuring human immunodeficiency virus-infected cells; a DNA encoding this polypeptide; a vector containing the DNA; a transformant obtained by transferring the vector into a host cell; a process for producing the polypeptide which is a constituent of a T cell receptor; transgenic animals having the polypeptide expressed therein; antibodies reacting specifically with the polypeptide; and anti-HIV agents containing the polypeptide which is a constituent of the killer T cell receptor.

BACKGROUND ART

Recently, there have been reports on the importance of a CD8 molecule-positive killer T cell involved in the initial phylaxis [Koup, R. A. et al., Nature, 370, 416 (1994)], delay in the development of AIDS [Levy, J. A. et al., Immunol. Today, 17, 217 (1996)] and resistance to the infection [Rowland-Jones, S. et al., Nature Med., 1, 59 (1995)] of human immunodeficiency virus (HIV), and further the HIV suppressive ability of a humoral factor secreted by the killer T cell [Cocchi, F. et al., Science, 270, 1811 (1995); Baier, M. et al., Nature, 378, 563 (1995)] have been reported.

Ho et al., reported that as a result of tracing with the viral loads of HIV-infected individuals and the immune responses induced by the virus with the elapse of time, the virus temporarily increased in vivo after infection but rapidly decreased as $CD8^+$ killer T cell precursor specific to the virus (cytotoxic T lymphocyte precursor; hereinafter referred to as CTL-p) appeared; and 6 to 8 weeks after that most of the viruses were cleared virus-specific IgG antibodies appeared. Thus the study suggested the importance of the cell-mediated immunity mainly with $CD8^+$ killer T cells in the initial phylaxis [Nature, 370, 416 (1994)].

Then, several articles reported that the presence of asymptomatic patients whose CD4 T cell counts have not decreased over ten and several years and who have not developed AIDS, and in these patients the cell-mediated immunity, in which CD8 positive T cells and Th1 type helper T cells are mainly involved, is dominant in vivo over the humoral immunity, and CD8 positive T cells secreting MIP-1 α, β [Science, 270, 1811 (1994)] or IL-16 [Nature, 378, 563 (1995)], capable of suppressing the proliferation of HIV, were identified. Thereafter the importance of the CD8 positive T cells including killer T cells and the cell-mediated immunity in the initial phylaxis and in the protection of the development of AIDS is increasingly noticed [Immunol. Today, 17, 217 (1996)].

The invasion of HIV into cells is, for example on T cells, regulated by fusin on the cell surface [Feng, Y. et al., Science, 272, 872 (1996)], and on macrophages, regulated by chemokine receptors, i.e., CC-CKR-5 [Deng, H. et al., Nature, 381, 661 (1996); Drajic, T. et al., Nature, 381, 667 (1996)]. It was reported that chemokines, i.e., MIP-1 α, β, or IL-16, binding specifically to a variety of chemokine receptors, inhibit the invasion of HIV into cells [Cocchi, F. et al., Science, 270, 1811 (1995); Bleul, C. C. et al., Nature, 382, 829 (1996)]. It was also reported that HIV-invasive sites are chemokine receptors, i.e., CC-CKR-4 or CC-CKR-5 [Science, 272, 872 (1996); Nature, 381, 661 (1996)] based on the fact that human races congenitally having a deletion in gene CC-CKR-5 escape from being infected with HIV [Nature, 382, 722 (1996); Cell, 86, 367 (1996)]. That is, it has been found that factors, e.g., MIP-1 α, β, and RANTES released by $CD8^+CTL$, block chemokine receptors so as to obstruct the invasion of HIV into cells, thereby suppressing the intracellular increase of HIV.

Moreover, it was shown that a part of the virus that invades via a chemokine receptor into a cell is HIV envelope protein gp160 V3 region [Nature, 384, 179 (1996); Nature, 384, 184 (1996)]. It is said that the HIV envelope protein gp160 V3 region determines the type of a cell, tropism infected with virus. Particularly, in a mouse, Env-K1 (or 18IIIB:RIQRGPGRAFVTIGKP18)[Takahashi, H. et al., Proc. Natl. Acad. Sci. USA, 85, 3105(1988)], the amino acid sequence 315 to 329 in the HIV envelope protein gp160 V3 region derived from HIV IIIB strain is presented on the cell surface together with Class I MHC molecule ($D^d$), and recognized by a specific killer T cell receptor [Takahashi, H. et al., J. Exp. Med., 170, 2023 (1989)]. At the same time, Env-K1 is presented on the cell surface together with Class I MHC molecules, HLA-A2, HLA-A3 and the like, which are recognized relatively widely in human, and the in vivo presence of killer T cells recognizing Env-K1 is confirmed in HIV-infected individuals [Clerici, M. et al., J. Immunol., 146, 2214 (1991); Dadaglio, G. et al., 147, 2302 (1991)].

When vaccinia virus recombined with HIV envelope (gp160) gene was inoculated in vivo into a healthy individual, killer T cells recognizing specifically ENV-K1 presented as an antigen by a variety of HLAs were induced, and the killer T cells specifically injured self-cells infected with the gp160 recombinant vaccinia virus [Achour, A. et al, Fifth International Conference on AIDS, p.546 (Abstract) (1989)]. However, killer T cell clones have not been produced.

Further, the V3 region within envelope gp160 including Env-K1 is known to be the recognition site of a neutralization antibody specific to HIV [Palker, T. J. et al., Proc. Natl. Acad. Sci. USA, 85, 1932 (1988); Rusche, J. R. et al., Proc. Natl. Acad. Sci. USA, 85, 3198 (1988); Goudsmit, J. et al., Proc. Natl. Acad. Sci. USA, 85, 4478 (1988)] or the recognition site of a helper T cell [Takahashi, H. et al., J. Exp. Med., 111, 579 (1990); Clerich, M. et al., Nature, 339, 383 (1989); Takeshita, T. et al., J. Immunol., 154, 1973 (1995)].

An anti-V3 antibody has a neutralizing activity against HIV. However, the anti-V3 antibody must be administered in vivo in a large quantity to suppress the proliferation of HIV. On the other hand, since an antibody is a macromolecule, such mass administration is undesirable. Therefore, establishing the killer T cell clone, which specifically recognizes V3, especially Env-K1, and detailed investigations of the molecular structure of the T cell receptor are considered to be useful in developing next generation agents for inhibiting the invasion of the virus by blocking the invasion of HIV.

Accordingly, it has been expected for the analysis of the HIV-specific killer T cell clone and for the development of a transgenic animal as an individual to express the functional receptor gene of such killer T cell to bring information extremely useful in treatment and researches for AIDS. However, so far neither such development nor analysis has not been reported.

It is required that HIV specific killer T cells be used in searching the fate of human immunodeficiency virus, and in developing treatment and pharmaceuticals for AIDS. Further it is also required to investigate how the previous expression of the gene can have an effect on the prevention of the infection, and how shutting the virus in, in which the gene are expressed after infection, can have an effect on the treatment. That is, there is a desire to analyze the CD8 positive killer T cell clone specifically injuring human immunodeficiency virus-infected cells and to develop a transgenic animal expressing the killer T cell receptor.

DISCLOSURE OF THE INVENTION

The present invention relates to (1) to (17) as shown below.

(1) A polypeptide which is a constituent of a killer T cell receptor and is capable of injuring specifically human immunodeficiency virus-infected cells;

(2) The polypeptide according to the above (1) wherein the human immunodeficiency virus is HIV-1;

(3) The polypeptide according to the above (2) wherein the HIV-1 is HIV-1 IIIB;

(4) The polypeptide according to any one of the above (1) to (3), wherein a polypeptide constitutes a killer T cell receptor which recognizes specifically human immunodeficiency virus envelope protein gp160.

(5) The polypeptide according to the above (4) wherein the recognition region of the killer T cell receptor which recognizes specifically human immunodeficiency virus envelope protein gp160 is a V3 region of the gp160;

(6) The polypeptide according to the above (5) wherein the recognition region is a region comprising the amino acid sequence 315 to 329 in the human immunodeficiency virus envelope protein gp160 V3 region;

(7) A polypeptide which comprises an amino acid sequence shown in SEQ ID NO: 7 or 9, or a polypeptide, which comprises an amino acid sequence wherein one or more of amino acids in the amino acid sequence are substituted, deleted or added, and is capable of injuring specifically human immunodeficiency virus infected-cells.

The above-mentioned substitutions, deletions or additions of one or more of amino acids can be performed by means of a well-known art before the filing of the present applicaiton, the site-directed mutagenesis method. In addition, the term "one or more of amino acids" used herein means the number of amino acids which can be substituted, deleted, or added by the site-directed mutagenesis method.

The polypeptide which comprises an amino acid sequence wherein one or more amino acids are substituted, deleted, or added, and is capable of injuring specifically human immunodeficiency virus-infected cells can be prepared according to the methods described in Molecular Cloning, A Laboratory Manual, Second Edition, Cold Spring Harbor Laboratory Press (1989) (hereinafter abbreviated as Molecular Cloning $_2$nd ed., ), Current Protocols in Molecular Biology, Supplement 1 to 38, John Wiley & Sons (1987–1997) (hereinafter abbreviated as Current Protocols in Molecular Biology), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488(1985), Proc. Natl. Acad. Sci. USA, 81, 5662 (1984), Science, 224, 1431(1984), PCT WO85/00817(1985), Nature, 316, 601(1985) and the like.

(8) A DNA encoding the polypeptide according to any one of the above (1) to (7).

(9) The DNA having the nucleotide sequence shown in SEQ ID NO:6 or 8.

(10) A DNA which encodes the polypeptide, capable of injuring specifically human immunodeficiency virus-infected cells, which can hybridize with the DNA according to the above (8) or (9) under stringent conditions.

As used herein, the term "the DNA which encodes the polypeptide, capable of injuring specifically human immunodeficiency virus-infected cells, which can hybridize under stringent conditions" means a DNA which can be obtained by using the DNA of the above (8) or (9) as a probe according to the colony hybridization technique, the plaque hybridization technique or the southern blot hybridization technique or the like. For example the DNA can be identified by performing hybridization using a filter, to which DNA derived from a colony or a plaque is immobilized, under the presence of 0.7 to 1.0M NaCl at 65° C. and then by washing the filter using 0.1–2×SSC (saline-sodium citrate) solution (where the composition of 1×SSC solution is 150 mM sodium chloride, 15 mM sodium citrate) at 65° C.

Hybridization can be performed according to the methods shown in protocols including Molecular Cloning $2^{nd}$ ed., Current Protocols in Molecular Biology, DNA Cloning 1: Core Techniques, A Practical Approach, Second Edition, Oxford University Press (1995), and the like.

The DNA which can be hybridized is, for example, a DNA having homology of 80% or more, preferably 95% or more, to the nucleotide sequence shown in SEQ ID NO: 6 or 8.

(11) A recombinant vector comprising the DNA according to any one of the above (8) to (10) and a vector.

(12) A transformant obtained by introducing the recombinant vector according to the above (11) into a host cell.

(13) A process of producing the polypeptide according to any one of the above (1) to (7), which comprises culturing the transformant of the above (12) in a medium, forming and accumulating the polypeptide of any one of the above (1) to (7) in the culture, and recovering the polypeptide from the culture.

(14) An antibody which specifically reacts with the polypeptide according to any one of the above (1) to (7).

(15) The polypeptide according to any one of the above (1) to (7), having a human type constant region site.

(16) Transgenic animals, having the polypeptide according to any one of the above (1) to (7) expressed therein.

(17) Anti-HIV agents containing the polypeptide according to any one of the above (1) to (7).

The killer T cell clone injuring HIV-infected cells can be established by preparing antigens, administering the antigens to animals for immunization, removing sensitized lymphocytes from the cells of the immunized animals and stimulating the sensitized lymphocytes.

As the HIV strain, which is used for producing the killer T cell clone injuring HIV infected cells, includes HIV-1 III3 strain or the like can be mentioned. As the epitope, Env-K1 containing the amino acid sequence 315 to 329 presented in V3 region within HIV-1 envelope protein gp160 [amino acid sequence; RIQRGPGRAFVTIGK (Takahashi, H. et al., Proc. Natl. Acad. Sci. USA, 85, 3105 (1988), hereinafter referred to as P18) can be mentioned.

The methods for administering the antigen include the following: a method using ISCOM (Immunostimulating complex) which is a special immunopotentiating substance (adjuvant) [Takahashi, H. et al., Nature, 344, 873 (1990)]; a method using a complex of QS-21, one of constituent of ISCOM, and HIV envelope protein gp160 [Wu, J. et al., J. Immunol., 148, 1438(1992)]; a method using a recombinant vaccinia virus wherein the gp160 gene is introduced

[Takahashi, H. et al., Proc. Natl. Acad. Sci. USA, 85, 3105 (1988)] and a method using self-dendritic cell formed by binding, a self-cell, into which the gp160 gene is introduced, and Env-K1 [Takahashi, H. et al., Int. Immuno., 5, 849 (1993)] since it is known to be difficult for general purified protein antigens and the like to induce the killer T cells.

Example of animals for immunization includes mice, rats, rabbits, monkeys and the like. For example, the mice for immunization have various genetic characters such as B10.PL(H-2$^u$), B10.P(H-2$^p$), B10.Q(H-2$^q$), and B10.A(H-2$^a$). In particular, a BALB/c(H-2$^d$) mouse which shows a high reactivity with P18 is preferred.

Sensitized lymphocytes are obtained by removing the spleen from the immunized animal, and performing a treatment such as the removal of erythrocytes. To stimulate the sensitized lymphocytes, antigen-presenting cells, fibroblasts and the like, which express antigens or to which antigens are bound, are irradiated with radiation or treated with mitomycin-C are used. These cells are preferably the same type of cell line as the immunized cells. P18 specific killer T cell clone can be established by stimulating continuously with the cells. The killer T cell clones injuring HIV infected-cells according to the present invention include RT-1, RT-2, RT-3 and the like. A method for confirming T cells is, e.g., FACScan using an antibody to a molecular marker expressed on the cell.

A T cell αβreceptor is a heterodimer protein formed by disulfide bonds of αchain and βchain polypeptides. The receptor forms a complex with CD3 and is expressed on the surface layer of a T cell. The specific T cella αβreceptor comprises many different V-(D)-J-C regions. The type of the receptor itself is considered to be defined according to the amino acid sequence of V region and the specificity to a foreign matter according mainly to the amino acid sequences of D and J regions. Accordingly, the T cell receptor gene is identified from P18-specific killer T cell clone by determining V regions for T cell receptor αchain and βchain, and by identifying the entire gene sequence.

The V regions of the T cell receptor αchain and βchain are identified by polymerase chain reaction (hereinafter referred to as PCR) with primers produced based on the sequences of the obtained mRNA and of each V region. Then the reverse transcription-PCR (RT-PCR) is performed for the obtained mRNA to produce cDNA. Thus the sequence can be determined.

The full-length DNA having a junctional region specific to p18 is produced by the recombinant PCR technique to determine the whole gene sequence.

The total RNA is prepared from the T cell clone by the guanidine thiocyanate—cesium trifluoroacetate method [Methods in Enzymology, 154, 3 (1987)], acidic guanidine thiocyanate-phenol-chloroform (AGPC) method [Analytical Biochemistry, 162, 156 (1987), Experimental Medicine 9, 1937 (1991)] and the like.

From the total RNA mRNA is prepared as poly (A)$^+$RNA according to the method using the oligo(dT) immobilized cellulose column technique (Molecular Cloning 2$^{nd}$ ed., ), the method using an oligo dT latex, and the like.

Alternatively, mRNA can be prepared directly from tissues or cells by using Fast Track mRNA Isolation Kit (manufactured by Invitrogen), Quick Prep mRNA Purification Kit (manufactured by Pharmacia), and the like.

From the total RNA or mRNA obtained, cDNA libraries are obtained by using conventional method.

For example the cDNA library can be prepared according to the method described in Molecular Cloning 2$^{nd}$ ed., Current Protocols in Molecular Biology, DNA Cloning 1: Core Techniques, A Practical Approach, Second Edition, Oxford University Press (1995) and the like, or by using commercially available kits, such as, SuperScript Plasmid System for cDNA Synthesis and Plasmid Cloning (manufactured by Gibco BRL) and ZAP-cDNA Synthesis Kit (manufactured by STRATAGENE).

As the cloning vectors for preparing the cDNA library, any of phage vectors and plasmid vector can be used so long as it is capable of autonomously replicating in *Escherichia coli* K12.

Examples of suitable vectors are ZAP Express [manufactured by STRATAGENE, Strategies, 5, 58 (1992)], pBluescript II SK(+) [Nucleic Acids Research, 17, 9494 (1989)], Lambda ZAP II (manufactured by STRATAGENE), λ gt10, λ gt11 [DNA Cloning, A Practical Approach, 1, 49 (1985)], λ TriplEx (manufactured by CLONTECH), λ ExCell (manufactured by Pharmacia), pT7T318U (manufactured by Pharmacia), pcD2 [Mol. Cell. Biol., 3, 280 (1983)], pUC18 [Gene, 33, 103 (1985)], and pAMo[J. Biol. Chem., 268, 22782–22787 (1993), another name, pAMoPRC3Sc (JP-A-05-336963)].

Any microorganism belonging to *Escherichia coli* can be used as a host microorganism. Examples of the host microorganisms are *Escherichia coli* XL1-Blue MRF' [manufactured by STRATAGENE, Strategies, 5, 81 (1992)], *Escherichia coli* C600 [Genetics, 39, 440 (1954)], *Escherichia coli* Y1088 [Science, 222, 778 (1983)], *Escherichia coli*Y1090 [Science, 222, 778 (1983)], *Escherichia coli* NM522 [J. Mol. Biol., 166, 1 (1983)], *Escherichia coli* K802 [J. Mol. Biol., 16, 118 (1966)], *Escherichia coli* JM105 [Gene, 38, 275 (1985)], *Escherichia coli* SOLR™ Strain (manufactured by STRATAGENE), and *Escherichia coli* LE392 (Molecular Cloning 2$^{nd}$ ed.,).

In addition to the cDNA library constructed by the above-mentioned methods, commercially available cDNA library can be used.

From the cDNA library constructed by the above-mentioned methods, the cDNA clone containing the DNA of the present invention can be selected the colony hybridization, or the plaque hybridization [Molecular Cloning 2$^{nd}$ ed.,] using probes labeled with isotope or fluorescence.

The probes can include a fragment obtained by amplifying a part of cDNA using PCR [PCR Protocols, Academic Press (1990)] with primers based on a partially known nucleotide sequence, and an oligonucleotide based on a partially known nucleotide sequence.

The primer prepared based on such sequences can be employed when both nucleotide sequences of the full-length cDNA on the 5'-end side and 3'-end side are known in sequences such as ESTs,.

cDNA is synthesized from the mRNA using the cDNA clone having the DNA of the present invention selected as described above, according to the above techniques.

By the use of 5'-RACE (rapid amplification of cDNA ends) and 3'-RACE [Proc. Natl. Acad. Sci. USA, 85, 8998 (1988)] wherein PCR is conducted with primers based on a nucleotide sequence of an adapter which is added to both ends of the cDNA and with those based on a partially known nucleotide sequence, cDNA which is upstream (5'-end side) and downstream (3'- end side) from the amplified fragment can be obtained.

The full-length DNA of the present invention can be obtained by ligating the obtained cDNA fragments.

To determine the nucleotide sequence of the DNA obtained by the above methods, the DNA fragments or those cleaved by an appropriate restriction enzyme(s) are introduced into a vector by standard techniques, then the product is analyzed by a standard nucleotide sequence analysis technique, e.g., the dideoxy technique by Sanger et al. [Proc. Natl. Acad. Sci. USA, 74, 5463 (1977)] or using nucleotide sequence analyzers of Perkin Elmer (373A.DNA sequencer), those of Pharmacia, and of LI-COR.

The DNA of interest can be prepared by chemical synthesis using a DNA synthesizer based on the nucleotide sequence information obtained by the above-mentioned methods. The DNA synthesizers include the one manufactured by Shimazu Corp. using the thiophosfite technique, the one (model 392) by Perkin Elmer using the phosphoamidite technique, and the like.

The novelty of the obtained nucleotide sequence can be confirmed by searching a nucleotide sequence database of GenBank, EMBL, DDBJ and the like, using a homology search program i.e., BLAST.

For a novel nucleotide sequence, after converting it to an amino acid sequence, an amino acid sequence database, e.g., GenPept, PIR, or Swiss-Prot, is searched using a homology search program e.g., FASTA, and Frame Search, thereby searching the existing genes having homologies.

The DNA of the present invention obtained by the above emthod can be expressed in a host cell to produce the polypeptide of the present invention, according to the methods described in Molecular Cloning $2^{nd}$ ed., Current protocols in Molecular Biology and the like.

That is, the polypeptide of the present invention can be produced by constructing a recombinant vector wherein the DNA of the present invention is inserted an appropriate expression vector at an insertion site located downstream of the promoter therein, transferring this vector to a host cell to obtain a transformant expressing the polypeptide of the present invention, and culturing this transformant.

As the host cells, any bacterial cells, yeast cells, animal cells, insect cells, plant cells and the like can be used, so long as the desired gene can be expressed therein. Particularly, a transformant obtained by transferring the recombinant vector, in which the DNA of the present invention is inserted to introduce into a peripheral blood cell of a healthy individual, can be employed for the gene therapy of HIV-infected individuals.

As the expression vectors, which are capable of autonomously replicating in the host cell or being integrated into a chromosome and contain a promoter at a site appropriate for the transcription of the DNA of the present invention are used.

When a prokaryote cell such as a bacterial cell is used as the host cell, the preferable recombinant vector expressing the polypeptide gene which is a constituent of a T cell receptor of the present invention can autonomously replicate in the prokaryotes and is a recombinant vector consisting of a promotor, ribosome binding sequence, the DNA of the present invention, and a transcription termination sequence. The vector may further comprise a gene requlating the promoter.

Examples of suitable expression vectors are pSE280 (manufactured by Invitrogen), pGEMEX-1 (manufactured by Promega), pQE-8 (manufactured by QIAGEN), pKYP10 (JP-A-58-110600), pKYP200[Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescript II SK(−) (STRATAGENE), pTrs30 (FERM BP-5407), pTrs32 (FERM BP-5408), pGHA2 (FERM BP-400), pGKA2 (FERM B-6798), pTerm2 (JP-A-3-22979, US4686191, US4939094, US5160735), pKK233-3 (manufactured by Amersham Pharmacia Biotech), pGEX (manufactured by Pharmacia), pET system (manufactured by Novagen), pSupex, pTrxFus (Invitrogen), and pMAL-c2 (New England Biolabs).

As the promoters, any promoters capable of being expressed in host cells can be used. When *Escherichia coli* is used as a host, promoters derived from such as *Escherichia coli* or phages include trp promotor (Ptrp), lac promotor (Plac), $P_L$ promoter, T7 promoter, $P_R$ promoter and the like. In addition, promoters, artificially designed and modified e.g., Ptrp×2 formed by joining two Ptrp in series, tac promoter, T7lac promoter, and let I promoter can be used. When *Bacillus subtilis* is used as a host, the promoters include SP01 and SP02 that are phages of *Bacillus subtilis*, penP promoters, and the like.

As the ribosome binding sequence, a plasmid in which the distance between Shine-Dalgarno sequence and a starting codon is appropriately adjusted (e.g., 6 to 18 bases) can be used preferably.

A transcription termination sequence is not always necessary for the expression of the DNA according to the present invention. Preferably, the transcription termination sequence is arranged directly after the structural gene.

Examples of suitable host cells are cells of microorganisms belonging to genus Escherichia, genus Serratia, genus Bacillus, genus Brevibacterium, genus Coryneabacterium, genus Microbacterium, genus Pseudomonas, for example, *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Serratia ficaria*, *Serratia fonticola*, *Serratia liquefaciens*, *Serratia marcescens*, *Bacillus subtilis*, *Bacillus amyloliquefaciens*, *Brevibacterium ammoniagenes*, *Brevibacterium immariophilum* ATCC14068, *Brevibacterium saccharolyticum* ATCC 14066, *Corynebacterium glutamicum* ATCC13032, *Corynebacterium glutamicum* ATCC14067, *Corynebacterium glutamicum* ATCC13869, *Corynebacterium acetoacidophilum* ATCC13870, *Microbacterium ammoniaphilum* ATCC15354, Pseudomonas sp. D-0110 and the like.

Introduction of the recombinant vector can be carried out by any of the method for introducing DNA into the above host cell, for example, the method using calcium ion [Proc. Natl. Acad. Sci. USA, 69, 2110 (1972)], the protoplast method (JP-A-63-248394), and the electroporation method [Gene, 17, 107 (1982), Molecular & General Genetics, 168, 111 (1979)].

As the plasmid containing the DNA encoding the polypeptide, which is a constituent of the killer T cell receptor of the present invention, for example, pH-RT1α containing the DNA encoding the killer T cell receptor αchain or pH-RT1β containing the DNA encoding the killer T cell receptor βchain, or the like can be mentioend. *Escherichia coli* TG1/pH-RT1α containing the plasmid pH-RT1α and *Escherichia coli* TG1/pH-RT1β containing the plasmid pH-RT1β were deposited with National Institute of Bioscience and Human-Technology, Agency of Industrial Science and Technology (1–3, Higashi-1-chome, Tsukuba-shi, Ibaraki-ken, Japan) as FERM BP-6078 and FERM BP-6079, respectively.

When a yeast cell is used as the host cell, YEp13 (ATCC37115), YEp24 (ATCC37051), YCp50 (ATCC37419), pHS19, pHS15 and the like can be used as the expression vectors.

As the promoter, any promoters capable of expressing in a yeast cell can be used. Examples of suitable promoters are PH05 promoter, PGK promoter, GAP promoter, ADH promoter, gal 1 promoter, gal 10 promoter, heat shock polypeptide promoter, MFα 1 promoter, and CUP 1 promoter.

The host cells can include yeast cells belonging to a genus Saccharomyces, genus Schizosaccharomyces, genus Kluyveromyces, genus Trichosporon, genus Schwanniomyces, genus Pichia, for example *Saccharomyces cerevisiae, Schizosaccharomyces pombe, Kluyveromyces lactis, Trichosporon pullulans, Schwanniomyces alluvius, Pichia pastoris,* and the like.

Introduction of the recombinant vector can be carried out by any of the methods for introducing DNA into yeast cells, for example the electroporation [Methods in Enzymology, 194, 182 (1990)], the spheroplast method[Proc. Natl. Acad. Sci. USA, 81, 4889 (1984)], and the lithium acetate method [Journal of Bacteriology, 153, 163 (1983)].

When an animal cell is used as a host cell, pcDNAI/Amp (manufactured by Invitrogen), pcDNAI, pAMoERC3Sc, pCDM8 [Nature, 329, 840 (1987)], pAGE107 [JP-A-3-22979, Cytotechnology, 3, 133 (1990)], pREP4 (manufactured by Invitrogen), pAGE103 [Journal of Biochemistry, 101, 1307 (1987)], pAMo, pAMoA, pAS3-3 (JP-A-2-227075) and the like can be used as the expression vector.

As the promotor, any promoters capable of expressing in animal cells can be used. Example of suitable promoters are cytomegalovirus (CMV) IE (immediate early) gene promoter, SV40 initial promoter or metallothionein promoter, retrovirus promoter, heat shock promoter, SR α promoter and the like. In addition, human CMV IE gene enhancer can be used with the promoter.

Examples of animal cells are mouse myeloma cells, rat myeloma cells, mouse hybridomas, human Namalwa cells, or Namalwa KJM-1 cells, human fetal kidney cells, human leukocytes, African green monkey kidney cells, Chinese hamster CHO cells, HBT5637 (JP-A-63-299) and the like.

The mouse myeloma cells include SP2/0, NS0 and the like, the rat myeloma cells include YB2/0 and the like, the human fetal kidney cells include HEK293 (ATCC: CRL-1573) and the like, the human leukocytes include BALL-1 and the like, and the African green monkey kidney cells include COS-1, COS-7 and the like.

Introduction of the recombinant vector can be carried out by any of the methods of introducing DNA into animal cells, for example the electroporation [Cytotechnology, 3, 133 (1990)], the calcium phosphate transfection (JP-A-2-227075), and the lipofection method [Proc. Natl. Acad. Sci. USA, 84, 7413 (1987)] and methods shown in Virology, 52, 456 (1973) and the like.

When an insect cell is used as a host cell, the polypeptide can be expressed by the methods described in Baculovirus Expression Vectors, A Laboratory Manual (W. H. Freeman and Company, New York (1992)), Molecular Biology, A Laboratory Manual, Current protocols in Molecular Biology, Bio/Technology, 6, 47 (1988) and the like.

That is, a recombinant vector for transferring a recombinant gene and baculovirus are co-introduced into an insect cell to obtain a recombinant virus in the insect cell culture supernatant, then the insect cell is infected with the recombinant virus, therefore the polypeptide can be expressed.

Examples of the gene transfer vector suitable for use in this method are pVL1392, pVL1393, and pBlueBacIII (both manufactured by Invitrogen).

An example of the Baculoviruses is *Autographa californica* nuclear polyhedrosis virus, which is a virus infecting insects belonging to family Barathra.

Examples of the insect cells are the ovarian cells of *Spodoptera frugiperda* and of *Trichoplusia ni,* culture cells derived from a silk worm ovarium.

The ovarian cells of *Spodoptera frugiperda* include Sf9, Sf21 (Baculovirus Expression Vectors, A Laboratory Manual) and the like, those of *Trichoplusia ni* include High 5, BTI-TN-5B1-4 (manufactured by Invitrogen) and the like, the culture cells from a silk worm ovarium include *Bombyx mori* N4 and the like.

Methods of transferring both said vector for transferring the recombinant gene and said baculovirus into an insect cell to prepare a recombinant virus include calcium phosphate transfection (JP-A-2-227075), lipofection [Proc. Natl. Acad. Sci. USA, 84, 7413 (1987)] and the like.

Methods of expressing genes include secretory production, fusion protein expression and the like according to the techniques shown in Molecular Cloning $2^{nd}$ ed in addition to direct expression.

When the gene is expressed in yeast cell, an animal cell, or insect cells, a sugar or sugar chain-attached protein can be obtained.

The polypeptide that is a constituent of a T cell receptor of the present invention can be produced by culturing the transformant obtained as described above to form the polypeptide that is a constituent of a killer T cell receptor of the present invention is formed, accumulated in the culture, and recovering the polypeptide accumulated in the culture.

Further, the polypeptide, which is a constituent of a T cell receptor of the present invention, can be expressed in vivo by transferring the expression vector to express the appropriate polypeptide, which is a constituent of a T cell receptor of the present invention, into a cell collected from a patient, and then by returning the cell into the body.

Culturing of the transformant of the present invention can be carried out by conventional methods for culturing the host cell of the transformant.

As the media for culturing of the transformant prepared by using microorganisms such as *Escherichia coli* or yeasts as a host cell, any of natural media and synthetic media can be used insofar as it contains a carbon source, a nitrogen source, and inorganic salts, and the like which can be assimilated by the microorganism used, and the transformant is efficiently cultured therein.

As the carbon sources, any glucose, fructose, sucrose, molasses, starch, carbonhydrates such as hydrolysates of starch, organic acids e.g., acetic acids and propionic acids, and alcohols e.g., ethanol and propanol can be used.

As the nitrogen sources any ammonia, salts of inorganic acids or organic acids, such as ammonium chloride, ammonium sulfate, ammonium acetate, and ammonium phosphate, other substances nitrogen containing compounds, peptone, meat extract, yeast extract, corn steep liquor, casein hydrolysates, soybean meal and soybean meal hydrolysate, various fermentation microorganic cells or their digests, and the like can be used.

The inorganic substances used in the present invention include potassium dihydrogenphosphate, dipotassium hydrogenphosphate, magnesium phosphate, magnesium sulfate, sodium chloride, ferrous sulfate, manganese sulfate, copper sulfate, calcium carbonate and the like.

Culturing is usually carried out under aerobic conditions, for example, by shaking cultures or submerged aeration stirring culture, at 15 to 40° C. for 16 to 96 hours. The pH is maintained at 3.0 to 9.0 during the culturing. The pH adjustment is carried out by using an inorganic or organic acid, alkaline solution, urea, calcium carbonate, ammonia, and the like.

If necessary, antibiotics such as ampicillin and tetracycline may be added to the medium.

When a microorganism transformed with the expression vector comprising an inducible promoter is cultured, an inducer may be added to the medium if necessary. For example isopropyl-β-D-thiogalactopyranoside (IPTG) or the like may be added in the case of microorganisms transformed with an expression vector comprising lac promoter, and in the case of microorganisms transformed with an expression vector comprising trp promoter, indoleacetic acid (IAA) or the like may be added.

For the culturing of the transformants prepared by using an animal cell as host cells include a generally used RPMI1640 media, Eagle MEM media or those to which fetal calf serum or the like is added may be used. Culturing is usually carried out in the presence of 5% $CO_2$ at 35 to 37° C. for 3 to 7 days. If necessary, antibiotics such as kanamycin and penicillin may be added to the medium while culturing.

For the culturing of the transformant prepared by using an insect cell as the host cell, TNM-FH medium (manufactured by Pharmingen), Sf900 II SFM (manufactured by Life Technologies), ExCell1400 and ExCell405 (both manufactured by JRH Biosciences) and the like may be used.

Culturing is usually carried out at 25 to 30° C., at a pH ranging from 6 to 7 and normally for 1 to 5 days. If necessary, antibiotics such as gentamicin may be added to the medium while culturing.

The polypeptide expressed in the above-described manner can be purified from the culture of the transformant by conventional methods for isolating and purifying enzymes to obtain the polypeptide which is a constituent of T cell receptor of the present invention.

For example, when the polypeptide of the present invention is expressed in a soluble form within the cell, after the completion of culturing and the cells are recovered by centrifugation, suspended in an aqueous buffer, followed by disruption using an ultrasonic disruption, a French press, a Manton Gaulin homogenizer, a Dyno Mill, and the like to obtain a cell-free extract.

The cell-free extract is centrifuged, and from the obtained supernatant, a purified sample can be produced from the supernatant obtained by centrifugation of the cell-free extract by conventional methods for isolating and purifying enzymes including a solvent extracting, salting-out with ammonium sulfate, desalting, precipitation with organic solvents, anion exchange chromatography using resins such as diethylaminoethyl (DEAE)—Sepharose and DIAION HPA-75 (manufactured by Mitsubishi Chemical Corp.), cation exchange chromatography using resins e.g., S-Sepharose FF (manufactured by Pharmacia) and the like, hydrophobic chromatography using resins such as butyl sepharose, phenyl sepharose and the like, gel filtration using molecular sieve, affinity chromatography, chromatofocusing, and electrophoresis such as isoelectric focusing, alone or in combination.

When the polypeptide is expressed in cells in an insoluble form, the cells are similarly disrupted, and separated by centrifugation, and fractions are precipitated, fraction. The polypeptide is recovered from the precipitate fraction by conventional method and the insoluble polypeptide is solubilized with a protein denaturing agent.

The solubilized solution is diluted or dialyzed to give a solution containing no protein-denaturing agent or containing protein-denaturing agent at a low concentration so that proteins are not denatured and the normal protein structure is restored, followed, by the same isolation and purification step as mentioned above to obtain a purified protein preparation.

When the polypeptide of the present invention or its derivatives such as a sugar-modified proteins are extracellularly secreted, the polypeptide or its derivatives such as the sugar chain-added from can be recovered from the culture supernatant.

That is, the culture is treated by the above-described means such as centrifugation, and the obtained soluble fractions is subjected to the same isolation and purification methods as described above to obtain a purified sample.

Further, the polypeptide of the present invention can be produced as a fusion protein with another protein and purified by affinity chromatography using substances having affinity for the fusion protein. For example according to the technique by Row et al., [Proc. Natl. Acad. Sci. USA, 86, 8227(1989), Genes Develop., 4, 1288 (1990)] or to methods described in JP-A-05-336963 and in JP-A-06-823021, the polypeptide of the present invention can be produced as a fusion protein with protein A, and purified by affinity chromatography using immunoglobulin G. Moreover, the polypeptide of the present invention can be produced as a fusion protein with a Flag peptide, and purified by affinity chromatography using an anti Flag antibody [Proc. Natl. Acad. Sci. USA, 86, 8227 (1989), Genes Develop., 4, 1288 (1990)]. Furthermore, the polypeptide of the present invention can be purified by affinity chromatography using an antibody specific to the polypeptide itself.

Moreover, the polypeptide of the present invention can be produced by chemical synthetic methods such as the Fmoc method (the fluorenylmethyloxycarbonyl method) and tBoc method (t-butyloxycarbonyl method) based on the amino acid sequence information contained in the polypeptide.

Further, the peptide of the present invention can be chemically synthesized by using peptide synthesizers manufactured by Advanced ChemTech, Perkin Elmer, Pharmacia, Protein Technology Instrument, Synthecell-Vega, PerSeptive, Shimazu Corp., and the like.

The structural analysis for the purified polypeptide of the present invention can be carried out by methods conventionally used in Protein Chemistry, for example by techniques shown in Protein Structure Analysis for Gene Cloning (Hisashi Hirano, Tokyo Kagaku Dojin, 1993).

The transgenic animals used herein means animals into which foreign genes are introduced at their initial developmental stage. The transgenic animals include mice, rats, or livestock such as cattle and sheep. The transgenic mouse is prepared as described below.

The transgenic mouse of the present invention can be prepared according to the methods of Hogan, B. et al., [Manipulating the mouse embryo. A laboratory manual. $2^{nd}$ ed. 1994. Cold Spring Harbor Laboratory Press, New York.] and Yamamura, K. et al., [J. Biochem., 9, 357–363 (1984)]. That is, a female C57BL/6 mouse treated with a hormone is allowed to cross, and the fertilized ovum is taken out, a fragment of a gene to be transferred but having no part of a vector, which is prepared in advance, is micro-injected using a micro-glass pipette into the male pronucleus of the fertilized ovum. Of the ova obtained to which the genes are introduced, several hundreds of surviving ova are transplanted into the uterine tubes of pseudo-pregnant mice, thereby generating transgenic mice. can be prepared as follows.

Animals are immunized using the proteins obtained by the above-mentioned method as antigens. For immunization the intact antigens may be administered subcutatenously, intravenously, or intraperitoneally to the animals. It is preferred to administer, the antigen in combination with a carrier protein with high antigenicity or an appropriate adjuvant.

The carrier proteins include Macroschisma sinense hemocyanin, Keyhole limpet hemocyanin, bovine serum albumin, bovine thyroglobulin and the like. The adjuvants include complete Freund's adjuvant, alminium hydroxide gel, pertussis vaccine and the like.

The animals for immunization include non-human mammals, including rats, goats, 3 to 20 weeks old mice, rats, hamsters and the like.

The antigen is administered 3 to 10 times every 1 to 2 weeks after the first administration. The dose of the antigen is preferably 50 to 100 μg per animal. On 3rd to 7th days after each administration, a blood sample is collected from fundus oculi veniplex, and the obtained serum is examined for reactivity to the antigen according to enzyme-linked immunosorbent assay [ELISA: IGAKU-SHOIN Ltd. (1976)] and the like.

Then non-human mammals, the serum of which shows a sufficient antibody titer, are employed as a source for serum- or antibody-producing cells.

The polyclonal antibodies can be prepared by subjecting the serum to separation and purification procedure.

The monoclonal antibody can be prepared by fusing the antibody-producing cells and a myeloma cells derived from a non-human mammal to obtain hybridoma, and culturing the obtained hydridoma or administering the obtained hybridoma to an animal to cause ascites tumor, and subjecting the culture or the ascites to isolation and purification steps.

The antibody-producing cells are collected from splenic cells, the lymph node, peripheral blood of a non-human mammal administered with the antigen.

As the myeloma cells, any myeloma cells capable of proliferating in vitro can be used. Examples of suitable cells lines are 8-azaguanine resistant mouse (derived from BALB/c) myeloma cell line P3-X63Ag8-U1 (P3-Ul) [G.Kohler et al.,; Europ. J. Immunol., 6, 511 (1976)], SP2/0-Ag14(SP-2) [M. Shulman et al., ; Nature, 276, 269 (1978)], P3-X63-Ag8653(653) [J. F. Kearney et al.,; J. Immunol., 123, 1548 (1979)], and P3-X63-Ag8(X63) [G.Kohler et al.,; Nature, 256, 495 (1975)] which is derived from a mouse. For culture or subculture of these cells, $2 \times 10^7$ or more of cells are secured before cell fusion according to Antibodies—A Laboratory Manual, Cold Spring Harbor Laboratory, 1988 (herein after abbreviated as A Laboratory Manual).

After the antibody producing cells obtained as described above and the myeloma cells are washed, a cell agglutination medium such as polyethylene glycol-1000 (PEG-1000) is added to fuse these cells, and then suspended in the medium. As the cell washing solution, examples of the solutions are an MEM medium, and a PBS (1.83 g of disodium hydrogenphosphate, 0.21 g of potassium dihydrogenphosphate, 7.65 g of sodium chloride, 1 l of distilled water, pH 7.2). As the medium used to suspend fusion cells, examples of the media are a HAT medium, which is an normal medium (RPMI-1640 medium to which 1.5 mM of glutamine, $5 \times 10^{-5}$M 2-mercaptoethanol, 10 μg/ml of gentamicin and 10% fetal calf serum (FCS) (manufactured by CSL) are added) supplemented with $10^{-4}$M hypoxantine, $1.5 \times 10^{-5}$ M thymidine and $4 \times 10^{-7}$M aminopterin, so that only the fusion cells of interest can be selectively obtained.

After the culturing, a portion of the culture supernatant is subjected to enzyme immunoassay, to select cells which react with an antigenic protein and do not react with an non-antigenic protein. Then cloning is carried out by limiting dilution, and cells showing a high and stable antibody titer according to enzyme immunoassay are selected as monoclonal antibody producing hybridoma cell lines.

Enzyme Immunoassay

Antigenic proteins or cells expressing antigenic proteins is coated on a 96-well plate and allowed to react with a primary antibody, namely a hybridoma culture supernatant or a purified antibody.

After the primary antibody reaction, the plate is washed and a secondary antibody are added.

The secondary antibody is an antibody obtained by labeling an antibody, which can recognize the immunoglobuline of the primary antibody with a biotin, an enzyme, a chemi-luminescent substance, a radioactive compound or the like. For example when a mouse is used to prepared hybriodmas, an antibody capable of recognizing the mouse immunoglobulin is used as the secondary antibody.

After the above-mentioned reaction is finished, a reaction suitable for a substance labeling the secondary antibody is performed, thereby selecting hybriodmas that produce monoclonal antibodies specifically reacting with the antigens.

The monoclonal antibodies can be prepared by separating and purifying from the culture fluid obtained by culturing the hymbridomas; or from the ascites of the 8 to 10 week mice or nude mice, which are treated with 0.5 ml Pristane (2,6,10,14-tetramethylpentadecane) by administering it intraperitoneally to the mice and are kept for 2 weeks, and to which the monoclonal antibody-producing hybridomas are administered so as to cause ascites tumor.

Monoclonal antibodies can be separated or purified by one or more of the methods including centrifugation, salting out using 40 to 50% saturated ammonium sulfate, caprylic acid precipitation method, chromatographies using DEAE-Sepharose column, anion exchange column, protein-A or -G column, or gel filtration column, and the like. The method allows to recover IgG or IgM fractions and obtain purified monoclonal antibodies.

BRIEF DESCRIPTION OF DRAWINGS

FIG. 12 shows the results of analysis of the expression of transgenes of RT-1 TCRαchain and βchain in a transgenic mouse. The expression of TCRαchain was confirmed by RT-PCR since there is no antibodies to TCRαchain. The thymus and spleen were removed from the transgenic mouse to extract mRNA, then RT-PCR was performed. As a result, a band corresponding to TCRαchain was shown in both tissues (upper Figure). For TCRβ chain, CD8$^+$T cell was analyzed by FACS using anti-Vβ 8 (F23.1) as a specific antibody (lower Figure).

BEST MODES FOR CARRYING OUT THE INVENTION

The present invention will be illustrated in detail as follows, but it is contemplated that the scope of the present invention is not limited thereto.

EXAMPLE 1

Establishment of P18 Specific Killer T Cell Clones (RT-1, RT-2, RT-3)

To establish P18 specific killer T cell clones (RT-1, RT-2, RT-3), BALB/c mice known to show high reactivity with P18 (H-2$^d$ haplotype) (6-week old, female) [PNAS, 85, 3105 (1988)] were immunized by administering via the tail vein recombinant vaccinia virus (10$^7$PFU per mouse) expressing a HIV-1 IIIB envelope protein gp160[Nature, 320, 535 (1986)]. Four weeks later, the spleens were removed from the immunized mice, and sensitized lymphocytes were prepared through steps including the removal of erythrocytes and the like. The sensitized lymphocytes were stimulated by antigen-presenting cells of homotypic cell line, which P18 were bound to and which were irradiated (3,300 rad), or by P18-expressing fibroblast cells of homotypic cell line [PNAS, 85, 3105 (1988)] (hereinafter referred to P18-expressing fibroblast), which is inactivated with mitomycin-C, thereby establishing a killer T cell line specifically injuring P18-bound cells. Further, limiting dilution is performed using a medium, RPMI1640 to which 10% FCS (fetal calf serum), 2 mM L-glutamine, 100 U/ml penicillin, 10 μg/ml streptomycin, 5×10$^{-5}$M 2-mercaptoethanol, and 10 mM HEPES buffer were added [hereinafter referred to as CTM (complete T cell medium)]. The medium containing killer T cells was dispensed to wells of a round-bottomed 96-well microtiter plate, each well containing 0.3 μl. The inactivated fibroblast cells, 10$^4$/well, were added to each well for re-stimulation. The half of the culture fluid was replaced with CTM containing 10% rat T-STIM (manufactured by Collaborative Research) every 3 to 4 days, and the continuous stimulation using the P18-expressing fibroblast was conducted once every two weeks, thereby to establish three P18 specific killer T cell clones (RT-1, RT-2, RT-3) from about 1000 wells (FIG. 1).

Figure 1:
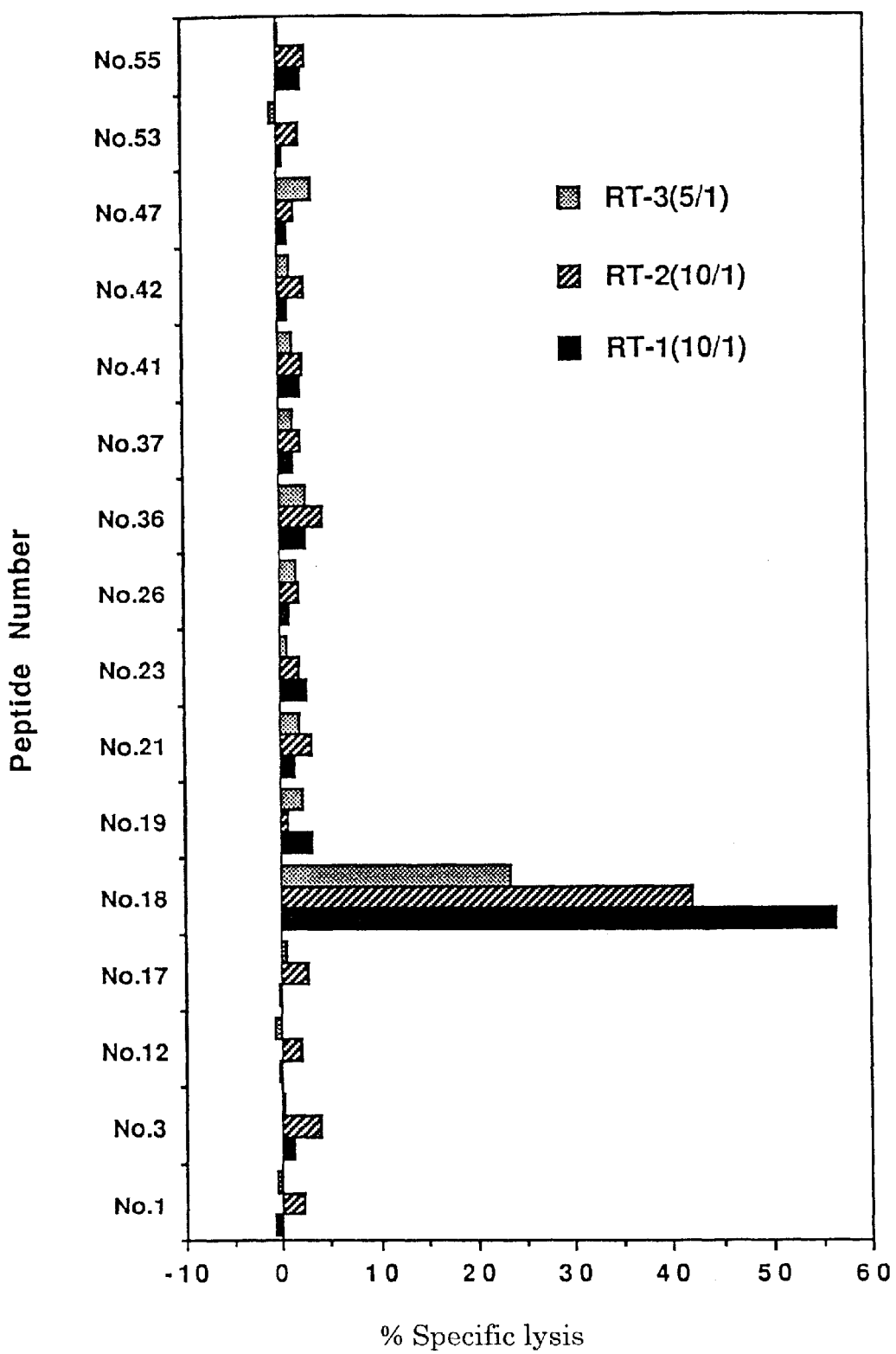
FIG. 1 shows the results of observation of which peptides are recognized by established T cell clones, RT-1, RT-2 and RT-3.

FIG. 1 shows results of observation as to which peptides were presented when various synthesized peptides (No. 1 to 55) covering HIV env were used. The results indicate that RT-1, RT-2 and RT-3 specifically recognized the cell to which P18 corresponding to No. 18 was bound. In addition it was confirmed that all of clones were killer T cells restrained by CD8 molecule-positive D$^α$ class I MHC molecule. The results are shown in FIGS. 2 and 3.

Figure 2:
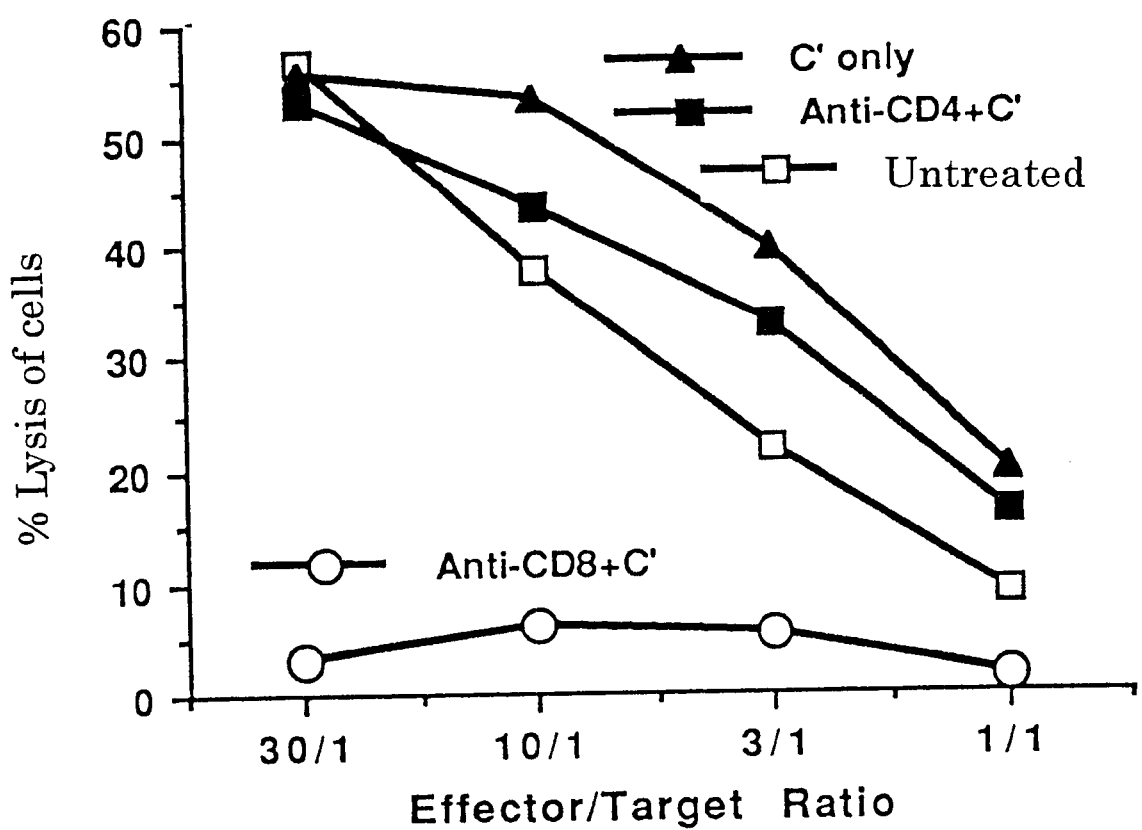
FIG. 2 is the graph showing changes in cytotoxic activity when the cell derived from the established killer T cell clone RT-1 is treated with 1) only complement, 2) complement and anti-CD8 antibody, 3) complement and anti-CD4 antibody, and 4) the cell is not treated.

FIG. 2 is a graph showing the changes in cytotoxic activity when the cell derived from the established killer T cell clone RT-1 was treated with 1) only complements, 2) complements and anti-CD8 antibody, 3) complements and anti-CD4 antibody, or 4) the cell was not treated. As shown in the graph, CD8$^+$T cell obviously has a P18 specific killer activity since the cytotoxic activity is removed by the treatment with the complement and anti-CD8 antibody.

Figure 3:
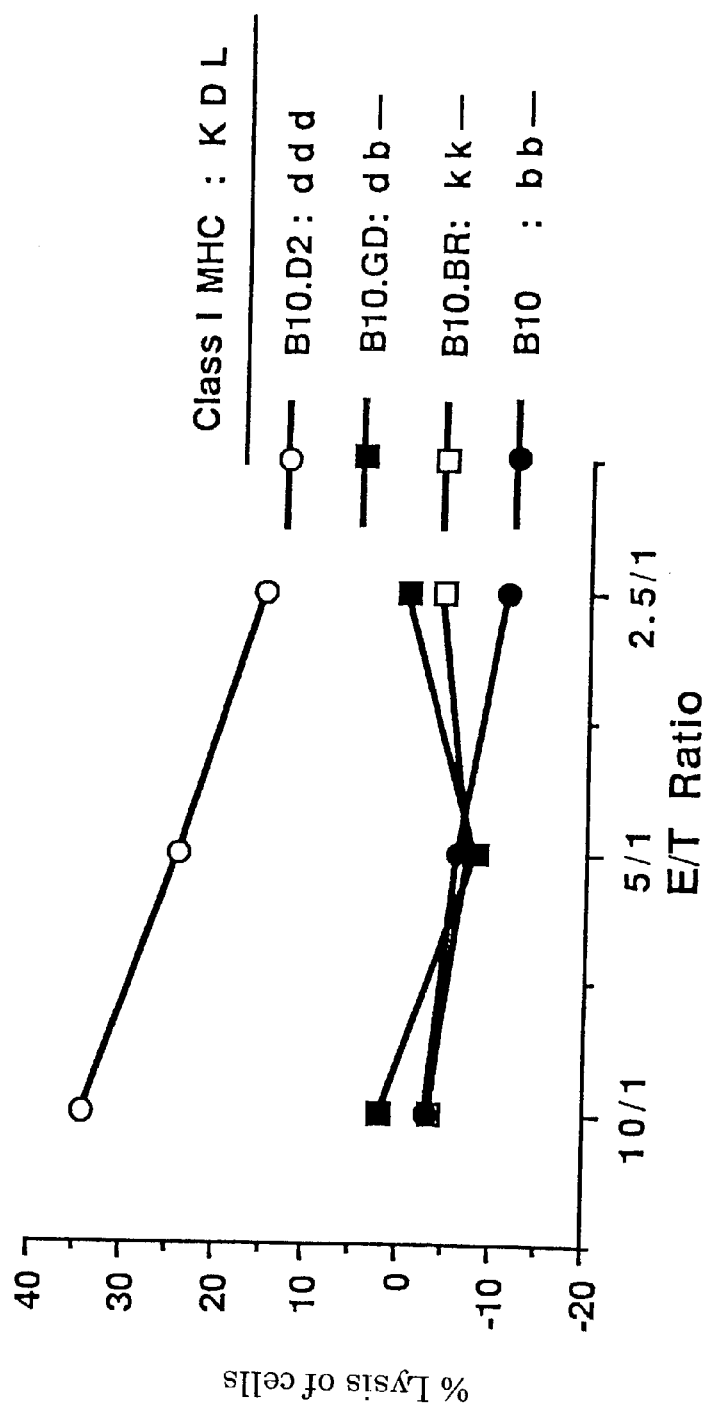
FIG. 3 shows the experimental results of studying: what type of class I MHC molecule is presented together with P18 for which the killer T cell clone RT-1 conduct specific recognization. Class I MHC:KDL means that in mice, class I MHC molecule presenting antigens comprises K, D, and L regions. For example in mice B10.D2, class I MHC molecule comprises $K^d$, $D^d$, and $L^d$ regions.

FIG. 3 shows results of study as to what type of class I MHC molecules is presented with P18 for which the killer T cell clone RT-1 conducts the specific recognition. In mice class I MHC molecules presenting antigens comprise K, D, and L regions. As shown in FIG. 3, the class I MHC molecules selectively recognize B10.D2 mouse that is restrained by D$^d$ and have cytotoxic activity. Therefore, it is suggested that the killer T cell clone RT-1 injures P18 by D$^d$ class MHC's restraint ability.

EXAMPLE 2

Isolation of T Cell Receptor Gene from P18-specific Killer T Cell Clone

V regions in P18-specific T cell receptor α- and β-chains were determined, followed by identification of gene sequences of each T cell receptor region.

1. Extraction of mRNA from P18-specific Killer T Cell Clone RT-1

The established P18-specific killer T cell clone, RT-1, having relatively strong proliferation potency and killer activity amoung the established P18 specific killer T cell clones, could be increased to $1\times10^8$ cells for about 6 months by repeatedly stimulating as described in Example 1. To efficiently extract mRNAs from $5\times10^7$ cell pellets, Fast TrackVersion2.0 mRNA Isolation (manufactured by Invitrogen) was used. As described below in steps a) to g), mRNAs were extracted using oligo-dT column from the lysate obtained by adding a surfactant agent.

a) Fifteen ml of a lysis buffer (which is 15 ml of stock buffer within the kit to which 0.3 ml of RNase protein degrader was added) was added to the cell pellet transferred to a 50 ml tube, then the mixture was stirred for 10 to 20 seconds.

b) The lysate obtained in a) was mixed using a 20 ml injection syringe with a 21 G needle, gently shaken in a thermostat at 45° C. for 60 minutes, thereby decomposing proteins and RNA degrading enzymes.

c) Fifteen ml of the mixture obtained in b) to which 0.95 ml of 5M NaCl was added was stirred well. After that one oligo(dT) tablet, which directly binds to mRNA and is attached to the kit, was put in the solution, then it was gently shaken for 60 minutes at room temperature.

d) The mixture was centrifuged at 2000 rpm for 5 minutes, and the supernatant was discarded. Twenty ml of a binding buffer within the kit was added to the pellet, the suspension was washed by centrifugation several times at 2000 rpm for 5 minutes, and then applied to an oligo-dT column.

e) The oligo-dT column to which 300 µl of low salt buffer was applied was repeatedly centrifuged at 5000 rpm for 10 seconds. After that a total of 400 µl of elution buffer was applied to the oligo-dT column, then the solution was centrifuged at 5000 rpm for 10 seconds, thereby obtaining a mRNA extract.

f) Sixty µl of 2M sodium acetate and 1150 µl of 100% ethanol were added to the mRNA extracts and stored in a freezer at −70° C. to −80° C. for a period of day and night.

g) An Eppendolf tube containing the mRNA pellet was centrifuged at 15000 rpm for several seconds, then, 50 µl of elution buffer was added to the pellet. The absorbance was measured at 260 nm to calculate the quantity of mRNA extracted, followed by experiments for determining T cell receptor sequences as shown below.

2. Determination of Type and Sequence of βChain

Figure 4:
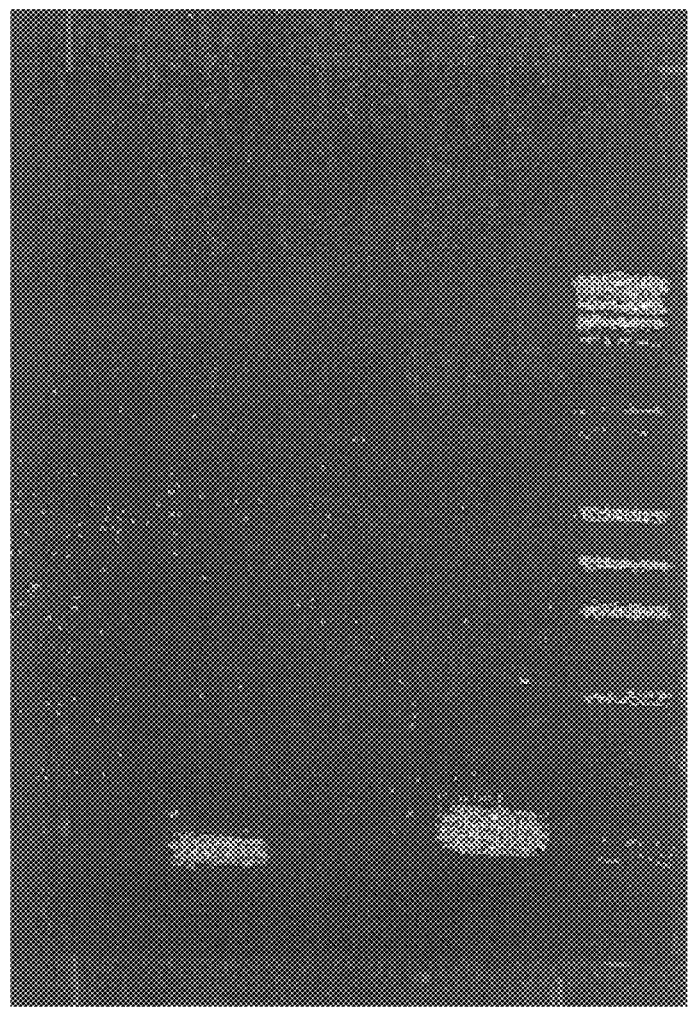
FIG. 4 shows the result that V β 8.1 DNA obtained from the killer T cell clone RT-1 amplified by PCR was confirmed by agarose gel eletrophoresis.
Figure 5:
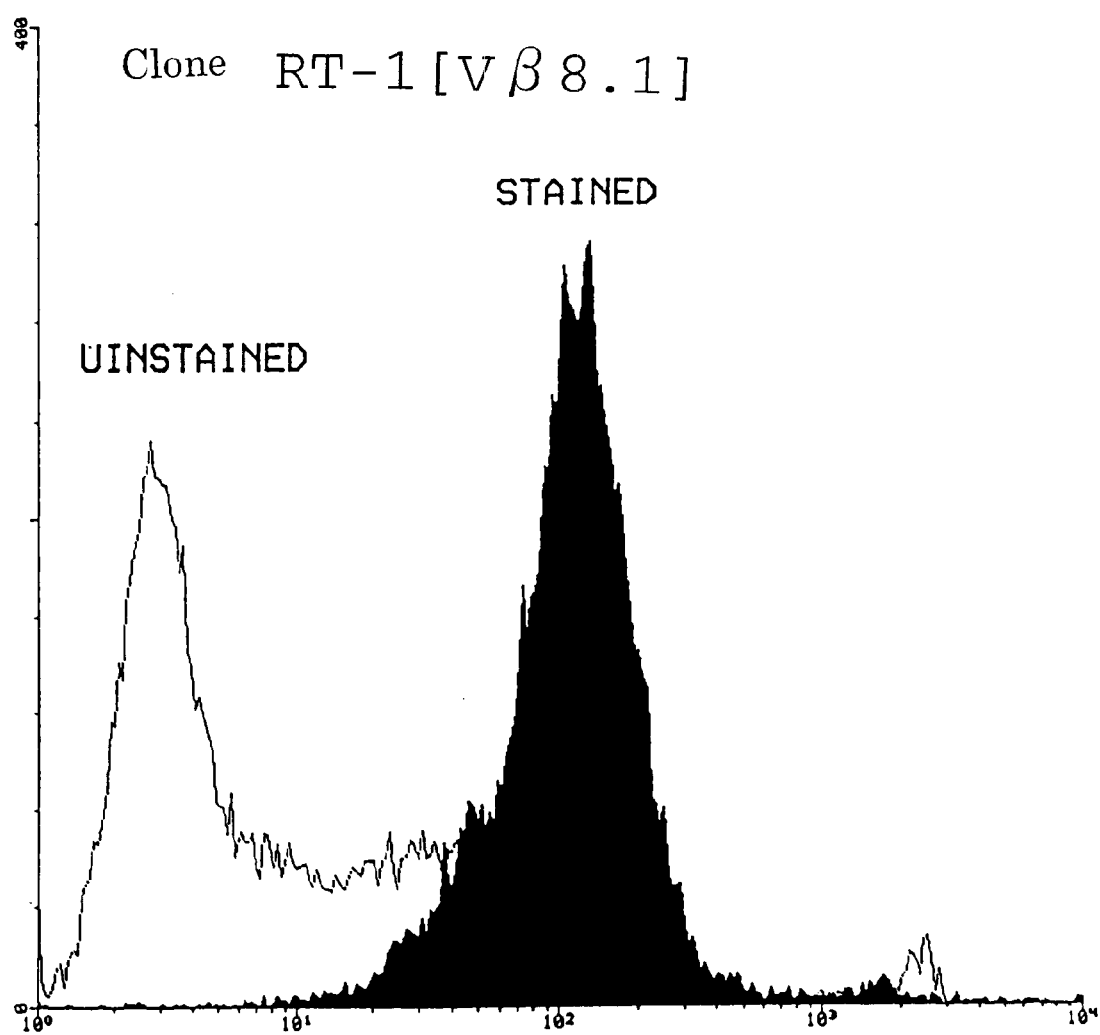
FIG. 5 shows the result of analysis of the T-cell clone RT-1 stained with anti-β 8.1 antibody using flow cytometry.

Unstable mRNA which is easily decomposed by RNase is easily converted to stable cDNA in the presence of reverse transcriptase and nucleic acids as a substrate. Analysis as follows was performed using GeneAmp RNA PCR Kit (manufactured by Perkin Elma Cetus) utilizing the above described fact. V region in a mouse T cell receptor βchain (hereinafter referred to as V β region) is either one of V β1 to V β17. To amplify mRNA derived from the clone, RT-PCR was performed using a primer group that was designed based on a characteristic sequence at each 5'-end and a primer (CB04E; SEQ ID NO: 2) that was designed based on a sequence of C region in the mouse T cell receptor (hereinafter referred to as Cβ region), common among all βchain. As a result of performing agarose gel eletrophoresis for the obtained samples, cDNA amplification was seen for V β8 primer (SEQ ID NO:1). Subsequently, to identify the subclass of V β8, nested PCR was performed using a combination of V β8 subclass primer having a sequence different from the primer used as described above and CB04E primer (SEQ ID NO:2). Agarose gel eletrophoresis was performed for the samples obtained so that amplification of cDNA was seen for V β8.1 primer (SEQ ID NO: 3) (FIG. 4). Further, RT-1 was stained with an anti V β8.1 antibody (manufactured by Farmingene) and flow cytometry was used, thereby confirming that V region of expressed T cell receptor βchain was β8.1(FIG. 5). Moreover, DNAs were recovered and purified from the PCR products. To the DNAs, DyeDeoxy Terminator was added and electrophoresis was performed. Then the T cell βchain gene sequence (SEQ ID NO: 6) was determined using a gene sequence automatic analyzer ABI (manufactured by Applied Biosystem).

Detailed explanation will be given as follows.

Four µl of 25 mM $MgCl_2$ solution, 2 µl of PCR buffer (×10), 2 µl each of dGTP, dATP, dTTP and dCTP, 1 µl of RNase inhibitor, 1 µl of reverse transcriptase, 1 µl of 3'-end primer (CB04E), and 2 µl of mRNA were added to a 0.5 ml microtube, and the solution was stirred using a voltex mixer for several seconds. After that one cycle of PCR (which consists of 42° C. for 15 min., 99° C. for 5 min., and 5° C. for 5 min.) was performed. Next, 4 µl of $MgCl_2$, 2 µl of PCR buffer (×10), 65.5 µl of distilled water, and 0.5 µl of AmpliTaq DNA polymerase solution were added to the PCR reaction solution while 2 µl of 5'-end primers (V β1 to V β17) were added to each sample. One cycle (95° C. for 2 min.,), 35 cycles (95° C. for 1 min., and 60° C. for 1 min.), and one cycle (5° C. for 7 min.) of PCR were performed.

Two% agarose gel eletrophoresis was performed for each of the obtained solutions corresponding to 5'-end primers (V β1 to V β17) so as to confirm the presence or absence of bands. As a result, a DNA band was confirmed between V β8 (SEQ ID NO:1) primer and CB04E (SEQ ID NO:2) primer.

Next, the PCR reaction solution (50 µl to 100 µl in total) containing βchain cDNA, which is obtained using RT-1 mRNA derived from RT-1, primer from 5' end of V β8.1 (SEQ ID NO:3), CB04E primer (SEQ ID NO:2) and reverse transcriptase was subjected to 1.0% agarose gel (SeaKem™ GTG Agarose) eletrophoresis followed by cutting the gel. The cut gel was dissolved in sodium iodide (NaI) solution, to which glass powder for recovering DNA (EASY TRAP TM Ver. 2, manufactured by Takara Shuzo Co., Ltd.) was then added. The mixture was left for 5 minutes at room temperature so as to allow DNA to adsorb. Then the mixture was washed with PBS, sterile distilled water or TE buffer was added to the pellet, and it was incubated at 55° C. for 5 minutes, thereby extracting DNA. Purified DNA in the supernatant was recovered, and the DNA gene sequence was determined. Methods employed are as shown below.

The primer from 5'-end (SEQ ID NO:3) of V β8.1 and CB04E primer (SEQ ID NO:2), 3.2 pmol each, were added to about 50 to 200 ng of the recovered DNA. Furthermore, deoxyribose, a terminator labeled with pigment and contained in Ready Reaction DyeDeoxy Terminator Cycle Sequencing Kit PRISM™ (manufactured by PERKIN ELMER CETUS), and AmpliTaq DNA polymerase and $H_2O$ were added to the DNA, and 25 cycles (where one cycle consists of 96° C. for 10 seconds, 50° C. for 5 seconds 60° C. for 4 minutes) of PCR were performed. The PCR product was applied to 6.75% Long Ranger™ Gel (manufactured by Takara Shuzo Co., Ltd.), electrophoresis was performed with about 40 watt for 14 hours, and the result was read using a gene sequence analyzer (ABI373 type, manufactured by Applied Biosystem), thereby determining the entire gene sequence. As a result, the nucleotide sequence for T cell receptor βchain of RT-1 was V β8.1-D β-J β2.1-C β2. The amino acid sequence for T cell receptor βchain of RT-1 was shown as SEQ ID NO: 7 and the nucleotide sequence as SEQ ID NO:6. *Escherichia coli* TG1/pH-RT1 β to which plasmid pH-RT1β containing DNA encoding T cell receptor βchain was transferred was deposited on Aug. 26, 1997 with National Institute of Bioscience and Human Technology, Agency of Industrial Science and Technology (1-3, Higashi 1-chome, Tsukuba-shi, Ibaraki-ken, Japan), and the assigned accession number was FERM BP-6079.

3. Determination of Type and Sequence of α Chain

Figure 6:
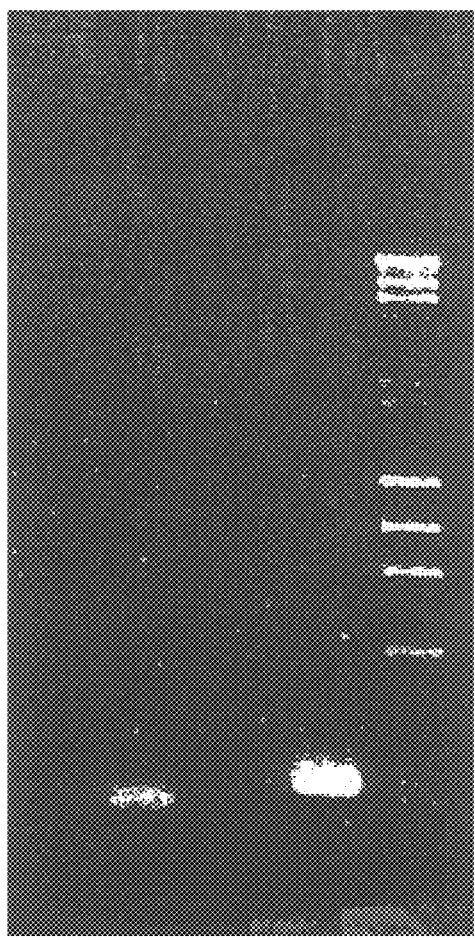
FIG. 6 shows the result that V α 42H11 DNA obtained from the killer T cell clone RT-1 amplified by PCR was confirmed by agarose gel eletrophoresis.

V regions in a mouse T cell receptor αchain (hereinafter referred to as V α region) containing 12 types of V regions ranging from V α1 to V α12 and their subtypes are known to be more complex than βchain such that there are about 80 types of V regions. MRNA derived from clone RT-1 was amplified by RT-PCR, as in the case for βchain, using a primer group designed based on their characteristic sequences and a primer of C β region, common among all αchains (exon-3 C α-R; SEQ ID NO:5) in the same manner as in Example 2.2. However no amplification occurred for any primer though the experiment was repeated. Therefore, unusual many V α primers were prepared based on database (GeneBank) and they were used to confirm amplification with V α42H11 primer (SEQ ID NO: 4). Next, nested PCR was performed using primers corresponding to various parts of V α42H11. After amplification, electrophoresis was performed and then bands were detected. Therefore it was confirmed that V α42H11 was a constituent of RT-1 (FIG. 6).

As in the case for βchain, the αchain cDNA was prepared using mRNA derived from RT-1, V α42H11 (SEQ ID NO:4), exon-3C α-R(SEQ ID NO:5), and reverse transcriptase and purified, to which dideoxyribose labeled with a pigment was added, and the gene sequence was determined using a gene sequence analyzer. As a result, the nucleotide sequence of T cell receptor αchain of RT-1 was V α42H11-J α25-C α. The amino acid sequence for T cell receptor αchain of RT-1 was shown as SEQ ID NO:9 and the nucleotide sequence as SEQ ID NO:8. *Escherichia coli* TG1/pH-RT1 α to which plasmid pH-RT1 α containing DNA encoding T cell receptor αchain was transferred was deposited on Aug. 26, 1997, with National Institute of Bioscience and Human Technology, Agency of Industrial Science and Technology (1-3, Higashi 1-chome, Tsukuba-shi, Ibaraki-ken, Japan), and the assigned accession number was FERM BP-6078.

EXAMPLE 3

Expression of T Cell Receptor and Functional Analysis

1. Preparation of Full-length cDNA of Clone RT-1 TCR αChain and βChain

The full-length cDNA clone was prepared to express the functional T cell receptor as described below.

A. T Cell Receptor αChain

Figure 7:
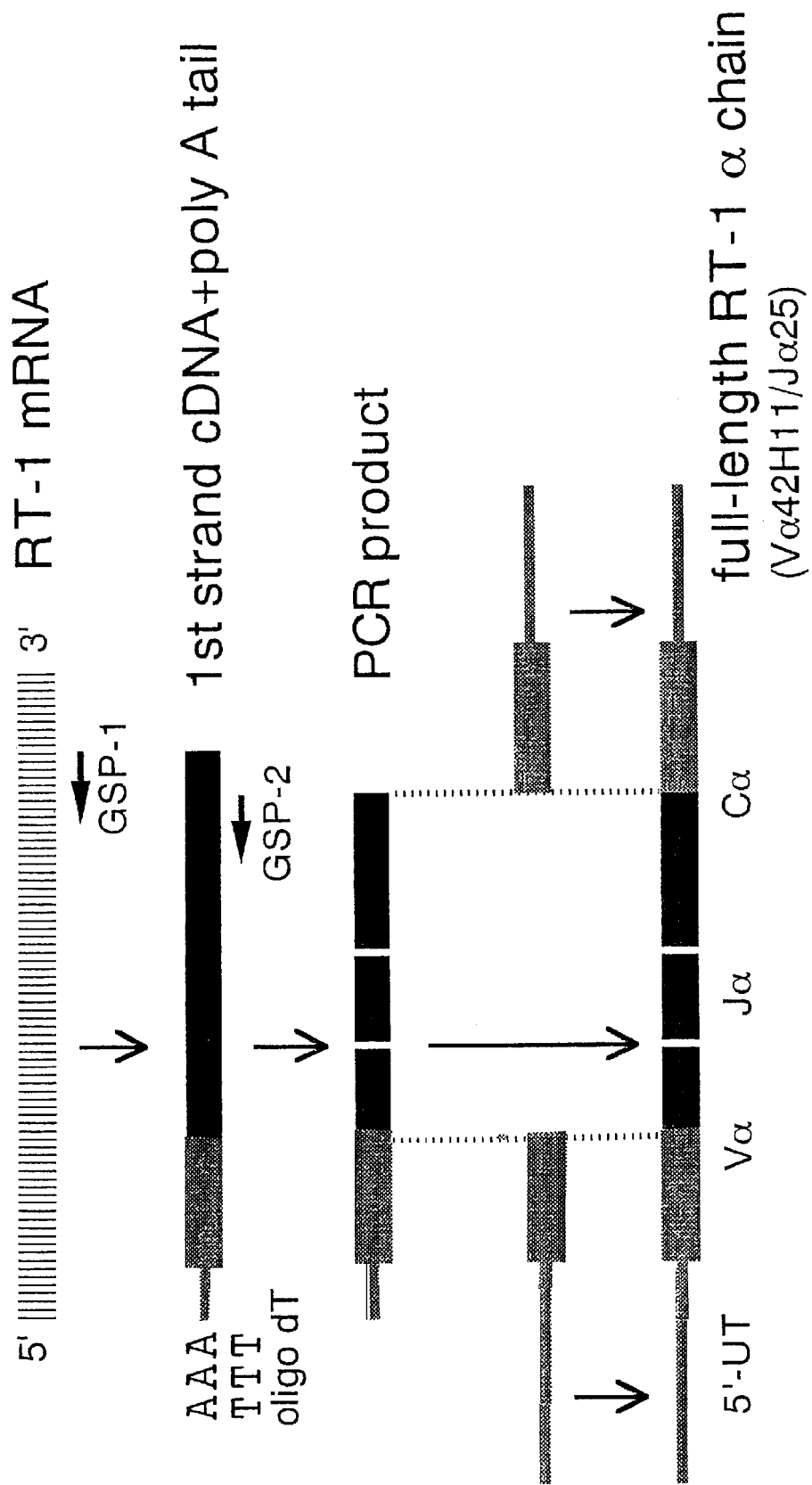
FIG. 7 is the construction of the full-length cDNA for the RT-1 TCR αchain. For αchain, V α was screened using 5' RACE method.

To obtain the full-length cDNA of αchain containing V α42H11 as shown in Example 2, DNA encoding VJC binding region (J region and parts of V and C regions at both ends of the J region) of the full-length cDNA derived from T cell clone specific to insulin using known V α42H11 [Mol. Cell. Biol., 7, 1865–1872(1987)] was substituted for DNA encoding RT-1 VJC binding region, thereby generating the full-length TCR αchain cDNA having a binding region specific to P18 (FIG. 7).

On the other hand, most T cell receptor αchains have several types of subfamilies in the identical V regions and a single T cell is known to express two αchains. Thus there are possibilities that V region sequence near the VJC binding part detected by PCR is a different subfamily of the identical family, having a variant at its 5' upstream even if it is identical to V α42H11, or that the sequence expresses another totally different αchain. Accordingly, cDNA at the upstream of C α was generated from RT-1 mRNA by 5' RACE method using a primer having an optional sequence of C α site(GSP-1 and GSP-2 as shown in FIG. 7) and an oligo dT primer, thereby determining the nucleotide sequence (SEQ ID NO:8). As a result, it was shown that most clones obtained had nucleotide sequences identical to V α42H11 itself. However, minor clones were shown to have αchain sequences that may be subfamilies (derived from insulin-specific T cell clone known as V α5.3.18) having a variation of two amino acids on the 5' side of V α[Mol. Cell. Biol., 7, 1865–1872 (1987)]. Amino acid sequence of T cell receptor αchain of RT-1 of the minor clones was shown as SEQ ID NO: 11, and the nucleotide sequence as SEQ ID NO: 10. The two can be considered to encode specific TCR αchain. Here, V α42H11 (amino acid sequence: SEQ ID NO: 9, nucleotide sequence; SEQ ID NO: 8) consistent with the major clones was considered to be T cell receptor αchain V α region which is specific to P18. The V α42H11 was expressed as follows.

B. T Cell Receptor βChain

Figure 8:
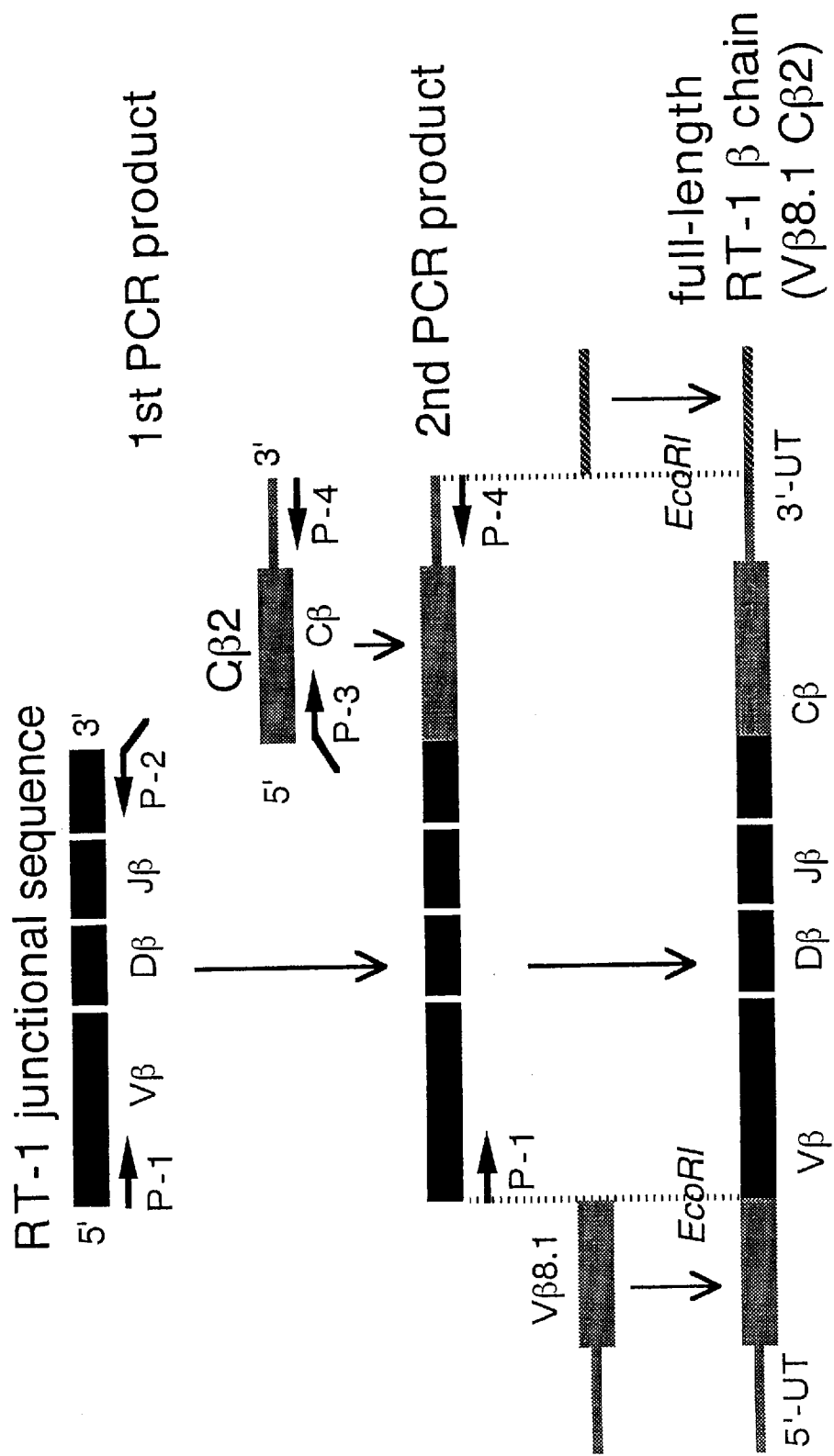
FIG. 8 is the construction of the full-length cDNA for RT-1 TCRβchain. For βchain, the PCR product of RT-1 junctional region was incorporated into βchain containing the known V β 8.1., using recombinant PCR.

Unlike V α region, V β region has no subfamily. 5' RACE method was performed without determining any sequence, V-D-J region and C region were amplified by RT-PCR and the resulting fragments were linked together to obtain full-length V β8.1. DNA encoding VDJC binding region (D-J region and parts of V and C regions at both ends of the D-J region) of the full-length TCR βchain cDNA (p14 TCR β) of the T cell clone specific to LCMV (lymphocytic choriomengitis virus) [EMBO J., 8, 719–727 (1989)] that expresses V β8.1 was substituted for DNA encoding RT-1 βchain VDJC binding region by recombinant PCR, thus generating the full-length TCR β cDNA (FIG. 8). The amino acid sequence was shown in SEQ ID NO: 7, and the nucleotide sequence in SEQ ID NO: 6.

Figure 9:
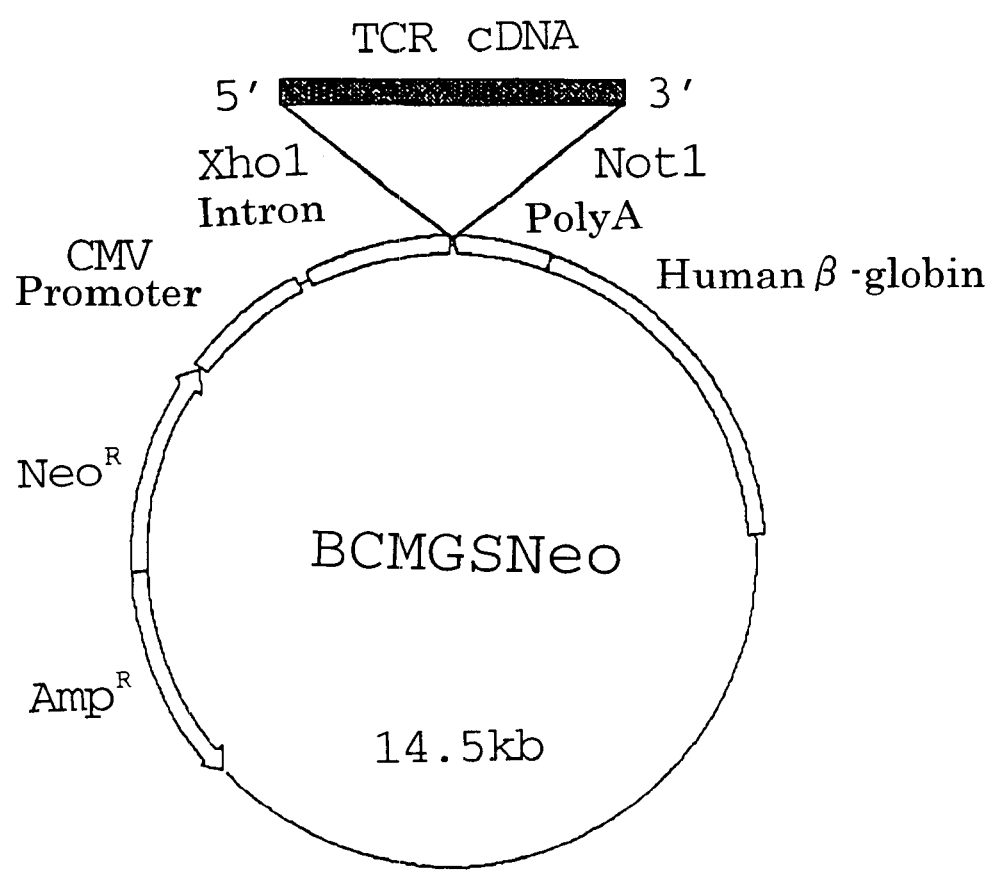
FIG. 9 shows the expression vector BCMGSNeo for in vitro transfection of RT-1TCRαchain and βchain.
Figure 10:
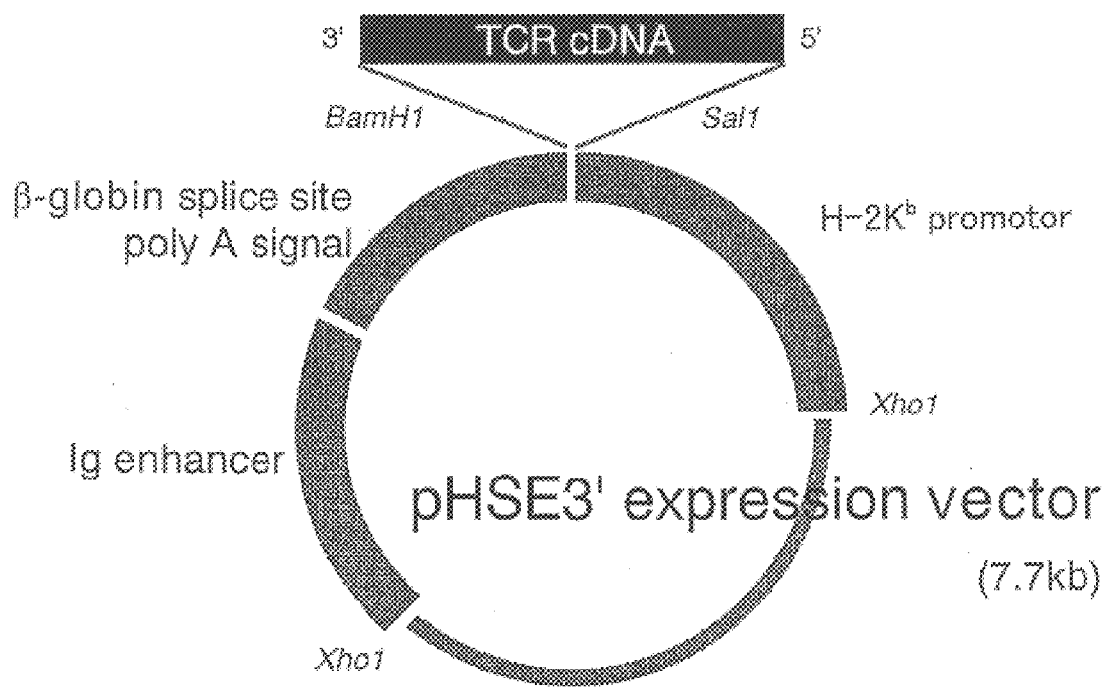
FIG. 10 shows the expression vector pHSE3' for transgenic of RT-1TCR αchain and βchain.

2. Generation of Expression Vectors for P18-specific T Cell Receptor α and βChain Genes After confirming the full-length cDNA gene sequences for P18 specific T cell receptor αchain (1.3 kb) and βchain (1.1 kb) both derived from RT-1 (obtained in Example 3.1), each of them was inserted into an expression vector. The expression vector BCMGS Neo [J.Exp. Med., 169, 13–25 (1989)] having a cytomegalovirus (CMV) promotor was employed for in vitro transfection into a cell line (FIG. 9). The expression vector pHSE3' [EMBO J., 8, 719–727 (1989)] having H-2K$^b$ promotor/Ig enhancer was employed for generating transgenic mice (FIG. 10). T cell receptor αchain (1.3 kb) and βchain (1.1 kb) were independently inserted at the XhoI site of the former vector, or inserted through blunt end ligation at BamH1/SalI sites of the latter vector, thus to generate recombinant vectors, BCMG-RT1 α, BCMG-RT1 β, pH-RT1 α and pH-RT1 β, respectively.

3. Transformation of RT-1 T Cell Receptor Gene into T Cell Line and in vitro Expression of the Gene BCMG-RT1 α and BCMG-RT1 β were transferred to a mutat T cell hybridoma TG40 [J. Immunol., 146, 3742–3746 (1991)], wherein gene coding for T cell receptor α and βchains is deleted, by eletroporation. The T cell receptor αβ requires CD8 as a conjugation receptor since it was derived from killer T cell. Then, the expression vector BCMGSNeo into which CD8 α and β genes were introduced was transferred to TG40 by electroporation. The expression of T cell receptor complex was confirmed by FACS staining using antibodies (F23.1, 2C11)(manufactured by Farmingene) specific to V β8.1 and CD3 ε. As a result, clones having both the CD8 and the T cell receptor expressed therein were obtained. The functional expression of the prepared full-length RT-1 TCR α and β chains were strongly suggested because they were activated by stimulating with anti-T cell receptor antibodies and because they were associated with CD3 complex.

EXAMPLE 4

Transgenic Mice Expressing RT-1 T Cell Receptor

1. Preparation of Transgenic Mice Expressing T Cell Receptors

Figure 11:
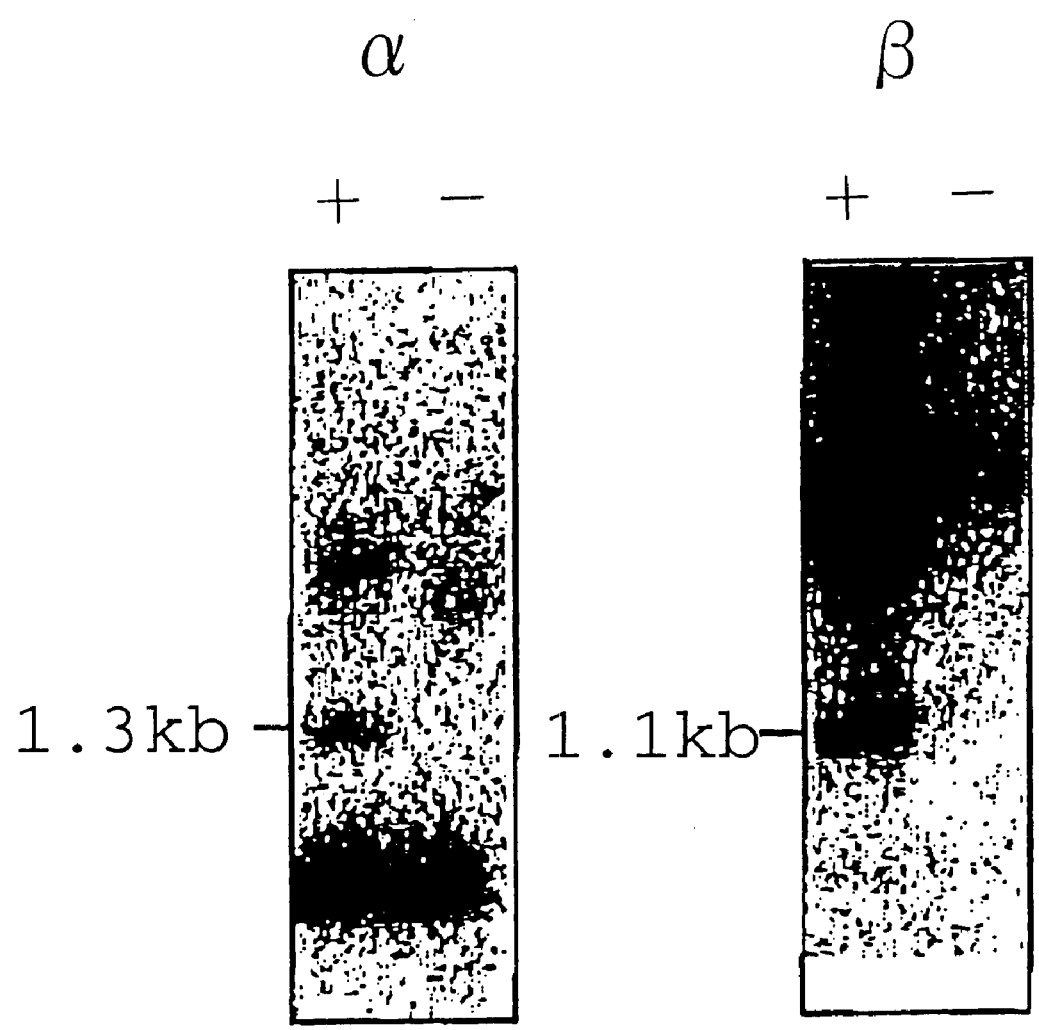
FIG. 11 shows the results of southern blot analysis for the transgenic mouse tail DNA of established TCRαchain and βchain.

After excluding vector portions of pH-RT1 α and pH-RT1 β which were independently created by introducing, DNA encoding T cell receptor αchain and βchain (hereinafter referred to as TCR α-DNA, and as TCR β-DNA, respectively) into pHSE3', the DNAs were micro-injected into fertilized ova of C57BL/6 (H-$2^b$) mice, alone or in combination. That is in the first cycle, TCR α-DNA and TCR β-DNA were separately, and in the second cycle, (TCR α-DNA) and (TCR β-DNA) together were injected. The tail DNA of mice born was prepared, and analyzed by PCR and Southern blotting. As shown in FIG. 11, it could be confirmed that transgenic mice in which TCR α and TCR β as transgenes were integrated, respectively, were obtained. These RT1TCR α- and RT1TCR β transgenic mice were crossed with wild type mice and further crossed with Balb/c mice. Since MHC genotype must be consistent with that of the original RT-1 clone, RT1TCR α and RT1TCR β, both having H-$2^d$ background, were so crossed that mice expressing RT1TCR αβ and having H-$2^d$ background were generated.

The expression of TCR α and β chains in the transgenic mice established as described above was examined. The results were shown in FIG. 12. For TCR βchain, it was found by fluorescent staining using anti-V β8 antibody (F23.1, manufactured by Farmingene) as described above that most of CD8 positive cells were V β$8^+$ in the transgenic mice, though in normal mice V β$8^+$ accounts for about 40%. On the other hand, the expression of TCR αchain was analyzed by RT-PCR wherein mRNA was expressed using primers corresponding to the binding region since there are no specific antibodies and staining cannot be performed. It was shown that almost no RT-1 TCR αchain was detected in the thymus and spleen cells of the normal mice, but it was highly expressed in those of the transgenic mice.

2. Function of HIVgp160env-specific TCR-transgenic Mouse

Figure 13:
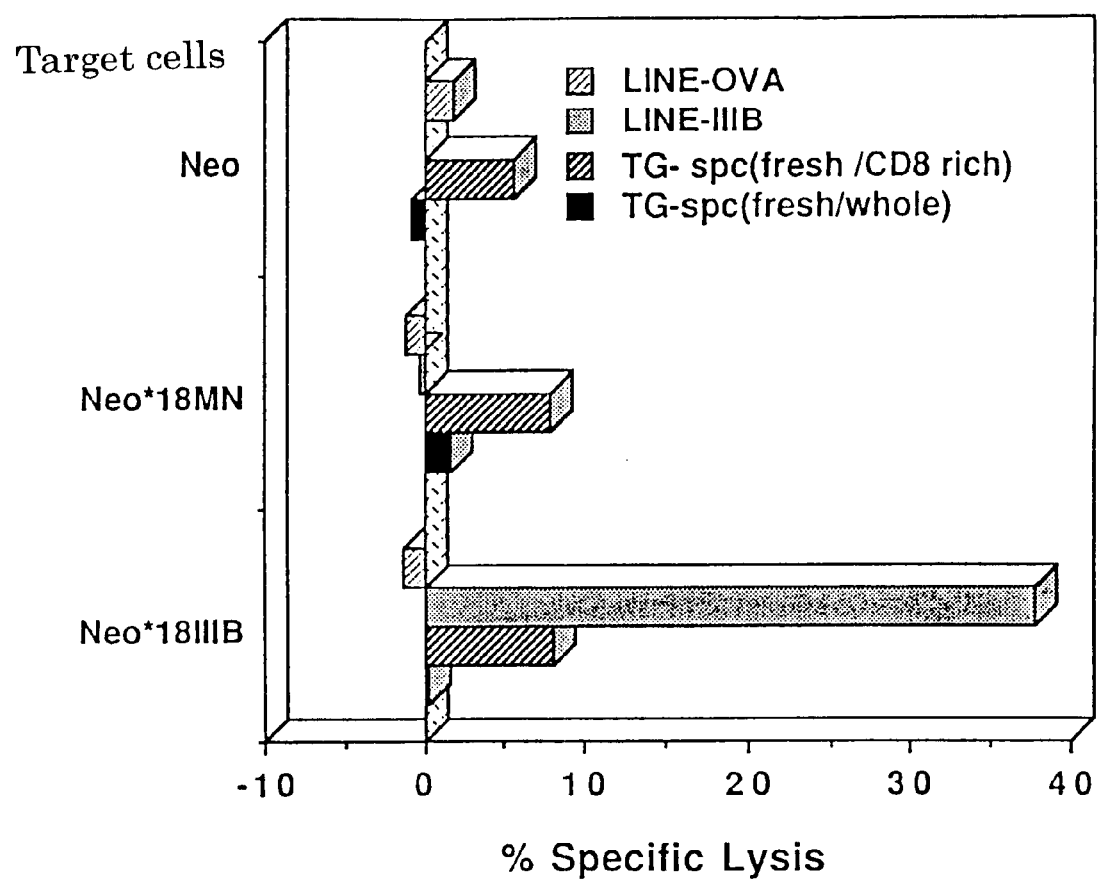
FIG. 13 is the graph showing the specific cytotoxic activity of cells derived from transgenic mice. LINE-OVA represents a T-cell line (negative control) reactive specifically with ovalbumin, LINE-IIIB represents a T-cell line (positive control) reactive specifically with HIV-IIIB strain, TG-spe (fresh/CD8 rich) is a spleen cell of the transgenic mice and represents an uncultured CD8+cell, and TG-spe (fresh/whole) is a spleen cell of the transgenic mice and represents the whole uncultured cell. As the target cells, Neo represents a Neo-gene-transferred BALB/c.3T3 cell (control cell), Neo*18MN represents a Neo-gene-transferred BALB/c.3T3 cell in which P18 peptide from HIV MN strain was pulsed, and Neo*18IIIB represents a Neo-gene-transferred BALB/c.3T3 cell in which P18 peptide derived from HIV-IIIB strain was pulsed.
Figure 14:
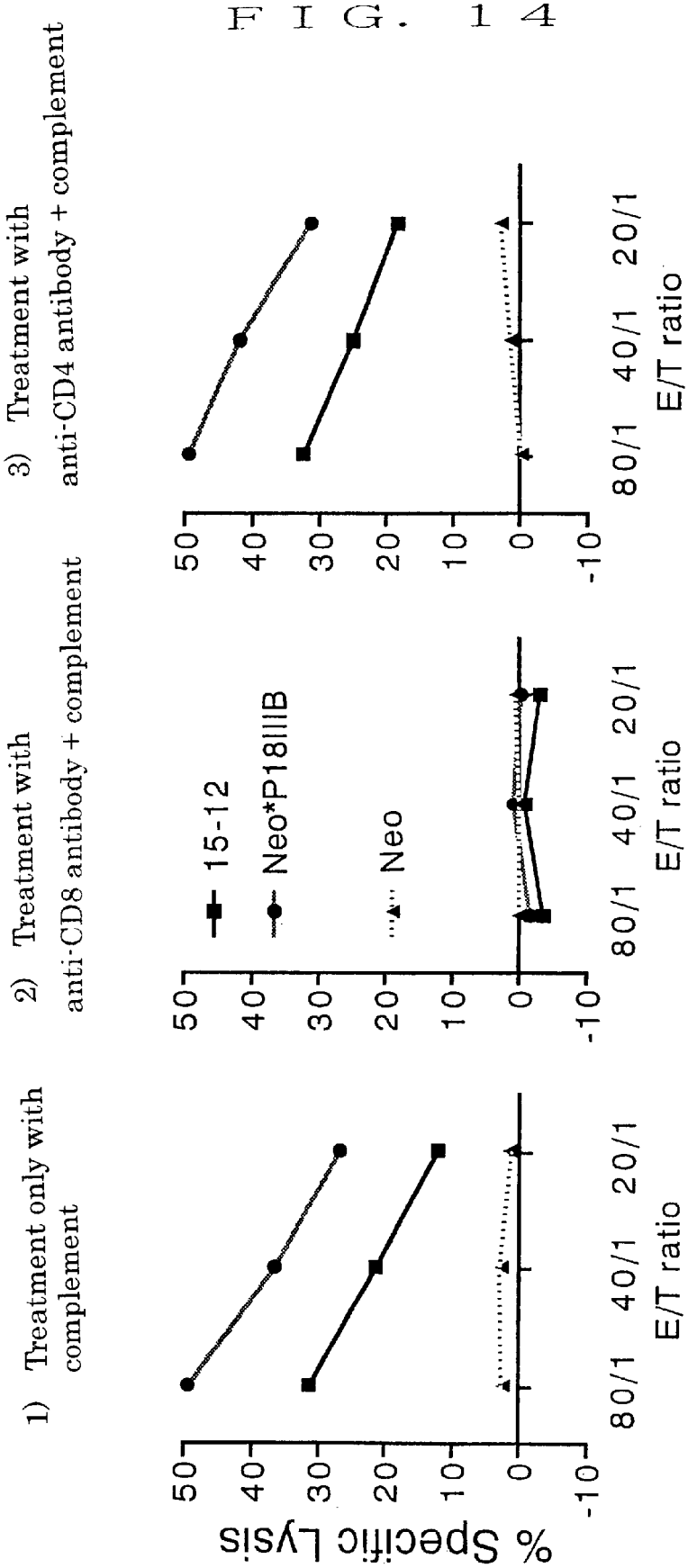
FIG. 14 is the graphs showing changes in the cytotoxic activity when cells derived from the transgenic mice were treated with 1) only complements, 2) complements and anti-CD8 antibody, or 3) complements and anti-CD4 antibody. 15-12 represents transfectant, which is a BALB/c. 3T3 cell into which HIV env gp160 gene was introduced, Neo*18IIIB represents a Neo-gene-transferred BALB/c.3T3 cell in which P18 peptide from HIV-IIIB strain was pulsed, and Neo represents a Neo gene-transferred BALB/c.3T3 cell. In 2) it is shown that CD8$^+$ T cell has a specific killer activity because of disappearance of the cytotoxic activity by treatment with the anti-CD8 antibody and complement.

Functions of the expressed TCR α and β were analyzed. The thymus and spleen cells were prepared from the mice expressing both TCR α and β, and their P18-specific cytotoxic activity was analyzed using an untreated group and a group in which CD8 positive cells were enriched. A transfectant into which P18 was previously transferred and a cell in which P18 was pulsed were used as target cells. As shown in FIG. 13, the results suggested that when compared to a specific CTL line as a positive control, no specific killer activity was found even if CD8$^+$ cells were enriched among cells directly separated from the transgenic mice. However when this separated cell group was re-stimulated by co-culturing with a homotypic cell line that HIV-1 gp160 gene was introduced into and expressed in vitro, P18-specific killer activity was observed as shown in FIG. 14. Furthermore, since this activity was removed by treating with the anti-CD8 antibody and complement, it was shown that CD8$^+$ T cells bear specific killer activity. That is as expected, RT-1TCR transgenic mice were shown to express killer T cells having HIVgp160-specific cytotoxic activity identical to that of the original RT-1.

EXAMPLE 5

Figure 15:
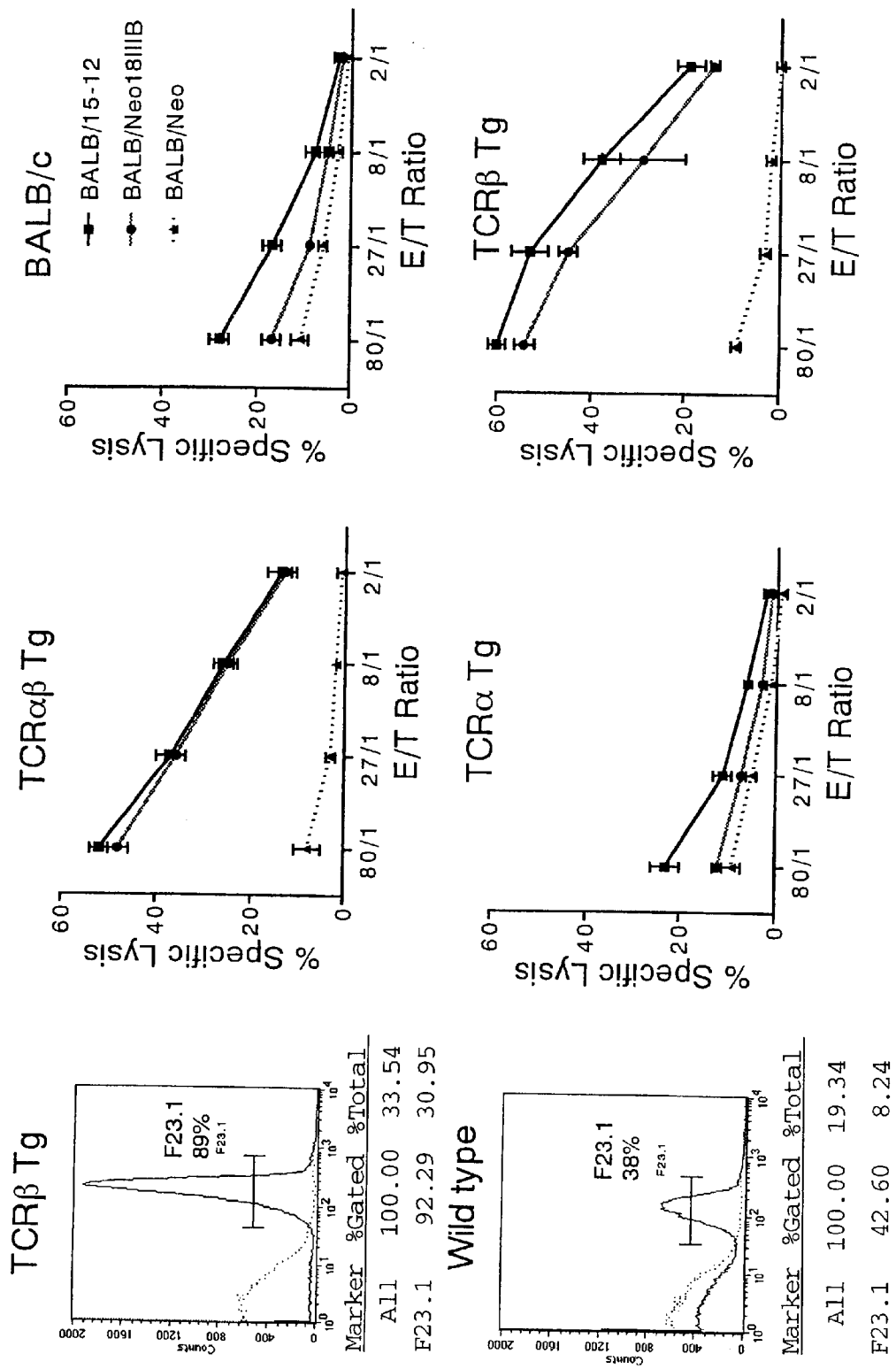
FIG. 15 shows cytotoxic activity which is induced, by stimulation of killer T cells after that spleen cells of various transgenic mice were stimulated with the transfectant (15-12) which is a BALB/c.3T3 cell into which HIV env gene was introduced, with 15-12, Neo gene-transferred BALB/c.3T3 cell in which P18 peptide derived from HIV-IIIB strain was pulsed(Neo*18IIIB), or BALB/c.3T3 cell into which Neo gene was introduced (Neo control cell). Cytotoxic activity was observed not only in TCRαβ expressing transgenic mice, but also in TCRβ expressing transgenic mice.
Figure 16:
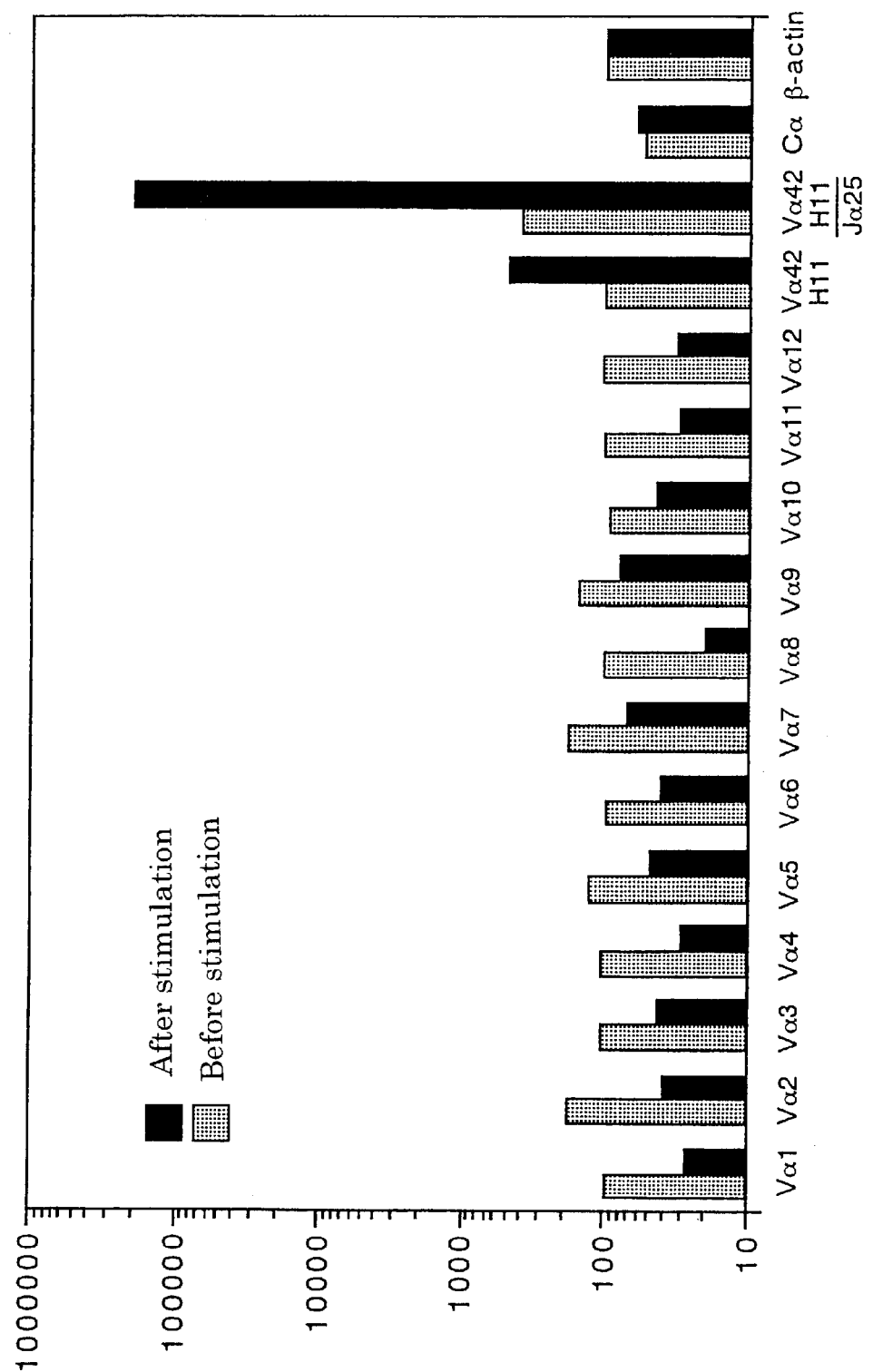
FIG. 16 shows the results of the study on α chain repertories (types) using RT-PCR before and after stimulation with HIV gp160 of TCRβ expressing transgenic mice having cytotoxic activity. Before the stimulation various type of the αchain were observed, but after the stimulation, a single type (V α 42H11J α 25) α chain was observed.

Induction of HIVgp160-specific Killer T Cells by HIVgp160specific-TCR βchain-transgenic Mice The transgenic mice which have expressed only TCR βchain were analyzed. It has been considered that normally specific recognition is performed only among TCR αβ-transgenic mice and no specific T cells are induced from transgenic mice expressing TCR βchain only or TCR αchain only because the recognition of antigens by T cells is performed by both TCR α and βchains. However as shown in FIG. 15, killer T cells specific to p18 peptide were induced by separating the spleen cells of the transgenic mice wherein HIVgp160-specific TCR βchain was expressed and by stimulating in vitro with cells expressing HIVgp160. Their antigenic specificity was identical to the original killer T cell clone RT-1 from which TCR was isolated. Then, the repertory of T cell TCR αchain induced by in vitro stimulation was examined by RT-PCR. As shown in FIG. 16, the results showed that before stimulation with HIVgp 160, T cell TCR αchain derived from TCR βchain-transgenic mice had random αchains, but after stimulation most of CD8$^+$T cells had TCR αchain completely consistent with that of RT-1. That is in HIVgp160-specific T cells, uniform p18-psecific killer T cells having TCR α and βchains identical to those of RT-1 can be induced not only by stimulating T cells having both TCR α and βchains but also by stimulating T cells having TCR βchain only.

Industrial Applicability

The present invention provides a polypeptide which is a constituent of a killer T cell receptor injuring specifically human immunodeficiency virus-infected cells, a DNA encoding said polypeptide, a vector containing said DNA, a transformant obtained by transforming with said vector, a process for producing said polypeptide which is a constituent of the T cell receptor, transgenic animals having said polypeptide expressed therein which is a constituent of the said killer T cell receptor, and an antibody to said polypeptide. The polypeptide which is a constituent of the killer T cell receptor, can be useful as anti-HIV agents.

Sequence Listing Free Text

SEQ ID NO:1: An oligonucletoide synthesized based on the T cell receptor V β8 sequence.

SEQ ID NO:2: An oligonuceotide synthesized based on the CB04E sequence.

SEQ ID NO:3: An oligonucleotide synthesized based on the T cell receptor V β8.1 sequence.

SEQ ID NO:4: An oligonucletide synthesized based on the T cell receptor V α 42H11 sequence.

SEQ ID NO:5: An oligonucleotide synthesized based on the exon-3C α-R sequence.

What is claimed is:

1. A polypeptide which is a constituent of a killer T cell receptor and is capable of specifically recognizing human immunodeficiency virus envelope protein gp 160.

2. The polypeptide according to claim 1 wherein the recognition region of the killer T cell receptor which specifically recognizes human immunodeficiency virus envelope protein gp160 is gp160V3 region.

3. The polypeptide according to claim 2, wherein the recognition region is a region comprising amino acid sequence 315 to 329 of V3 region of human immunodeficiency virus envelope protein gp160.

4. A polypeptide which comprises an amino acid sequence shown in SEQ ID NO: 7 or 9, or a polypeptide which comprises an amino acid sequence wherein one or more of amino acids in the amino acid sequence are substituted, deleted or added, and is capable of specifically recognizing human immunodeficiency virus envelope protein gp 160.

5. A DNA encoding the polypeptide according to claim 1 or 4.

6. A DNA having a nucleotide sequence shown in SEQ ID NO: 6 or 8.

7. A process for producing the polypeptide according to claim 1 or 4, which comprises culturing on a medium a transformant comprising a host cell harboring a vector comprising DNA encoding said polypeptide, forming and accumulating the polypeptide in the culture, and then recovering the polypeptide from the culture.

8. An antibody which specifically reacted with the polypeptide according to claim 1 or 4.

9. The polypeptide according to claim 1 or 4, having a human type constant region site.

10. Transgenic animals having the polypeptide according to claim 1 or 4 expressed therein.

11. Anti-HIV agents containing the polypeptide according to claim 1 or 4.

12. A DNA which encodes a polypeptide, capable of recognizing specifically human immunodeficiency virus envelope protein gp160, which can hybridize with a DNA encoding the polypeptide according to claim 1 under stringent conditions.

13. A DNA which encodes a polypeptide, capable of recognizing specifically human immunodeficiency virus envelope protein gp 160, which can hybridize with a DNA encoding the polypeptide according to claim 4 under stringent conditions.

14. A recombinant vector comprising the DNA according to claim 5 and a vector.

15. A recombinant vector comprising the DNA according to claim 6 and a vector.

16. A recombinant vector comprising the DNA according to claim 12 and a vector.

17. A recombinant vector comprising the DNA according to claim 13 and a vector.

18. A transformant obtained by introducing the recombinant vector according to claim 14 into a host cell.

19. A transformant obtained by introducing the recombinant vector according to claim 15 into a host cell.

20. A transformant obtained by introducing the recombinant vector according to claim 16 into a host cell.

21. A transformant obtained by introducing the recombinant vector according to claim 17 into a host cell.

22. A method for treating HIV-infected individuals comprising administering a therapeutically effective amount of the transformant according to claim 18 to a patient.

23. A method for treating HIV-infected individuals comprising administering a therapeutically effective amount of the transformant according to claim 19 to a patient.

24. A method for treating HIV-infected individuals comprising administering a therapeutically effective amount of the transformant according to claim 20 to a patient.

25. A method for treating HIV-infected individuals comprising administering a therapeutically effective amount of the transformant according to claim 21 to a patient.

* * * * *

SEQUENCE LISTING

<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: Designed oligonucleotide based on the sequence
      of VYA8 of T cell receptor

<400> SEQUENCE: 1
atatccctga tgggtacaag g                                          21

<210> SEQ ID NO 2
<211> LENGTH: 27
<212> TYPE: DNA
<213> ORGANISM: Artificial Sequence
<220> FEATURE:
<223> OTHER INFORMATION: Designed oligonucleotide based on the sequence
      of CB04E

<400> SEQUENCE: 2
ccgatgggag cacacgaacc cttaagc                                    27

<210> SEQ ID NO 3
<211> LENGTH: 21
<212> TYPE: DNA
<213> ORGANISM: Artificial Sequence
<220> FEATURE:
<223> OTHER INFORMATION: Designed oligonucleotide based on the sequence
      of VYA8.1 of T cell receptor

<400> SEQUENCE: 3
atgggctcca gactcttctt t                                          21

<210> SEQ ID NO 4
<211> LENGTH: 20
<212> TYPE: DNA
<213> ORGANISM: Artificial Sequence
<220> FEATURE:
<223> OTHER INFORMATION: Designed oligonucleotide based on the sequence
      of VY"42H11 of T cell receptor

<400> SEQUENCE: 4
atggactgtg tgtatgaaac                                            20

<210> SEQ ID NO 5
<211> LENGTH: 22
<212> TYPE: DNA
<213> ORGANISM: Artificial Sequence
<220> FEATURE:
<223> OTHER INFORMATION: Designed oligonucleotide based on the sequence
      of exon-3CY"-R

<400> SEQUENCE: 5
actggaccac agcctcagcg tc                                         22

<210> SEQ ID NO 6
<211> LENGTH: 912
<212> TYPE: DNA
<213> ORGANISM: Mus musculus
<220> FEATURE:
<221> NAME/KEY: CDS
<222> LOCATION: (1)..(909)
<221> NAME/KEY: sig_peptide
<222> LOCATION: (1)..(54)

```
<221> NAME/KEY: mat_peptide
<222> LOCATION: (55)..(909)

<400> SEQUENCE: 6 atg ggc tcc aga ctc ttc ttt gtg gtt ttg att ctc ctg tgt gca aaa      48
Met Gly Ser Arg Leu Phe Phe Val Val Leu Ile Leu Leu Cys Ala Lys
            -15             -10                  -5 cac atg gag gct gca gtc acc caa agt cca aga agc aag gtg gca gta      96
His Met Glu Ala Ala Val Thr Gln Ser Pro Arg Ser Lys Val Ala Val
 -1   1               5                  10 aca gga gga aag gtg aca ttg agc tgt cac cag act aat aac cat gac     144
Thr Gly Gly Lys Val Thr Leu Ser Cys His Gln Thr Asn Asn His Asp
 15              20                  25                  30 tat atg tac tgg tat cgg cag gac acg ggg cat ggg ctg agg ctg atc     192
Tyr Met Tyr Trp Tyr Arg Gln Asp Thr Gly His Gly Leu Arg Leu Ile
                 35                  40                  45 cat tac tca tat gtc gct gac agc acg gag aaa gga gat atc cct gat     240
His Tyr Ser Tyr Val Ala Asp Ser Thr Glu Lys Gly Asp Ile Pro Asp
             50                  55                  60 ggg tac aag gcc tcc aga cca agc caa gag aat ttc tct ctc att ctg     288
Gly Tyr Lys Ala Ser Arg Pro Ser Gln Glu Asn Phe Ser Leu Ile Leu
         65                  70                  75 gag ttg gct tcc ctt tct cag aca gct gta tat ttc tgt gcc agc agt     336
Glu Leu Ala Ser Leu Ser Gln Thr Ala Val Tyr Phe Cys Ala Ser Ser
     80                  85                  90 gag ggg aga gag gct gag cag ttc ttc gga cca ggg aca cga ctc acc     384
Glu Gly Arg Glu Ala Glu Gln Phe Phe Gly Pro Gly Thr Arg Leu Thr
 95                 100                 105                 110 gtc cta gag gat ctg aga aat gtg act cca ccc aag gtc tcc ttg ttt     432
Val Leu Glu Asp Leu Arg Asn Val Thr Pro Pro Lys Val Ser Leu Phe
                115                 120                 125 gag cca tca aaa gca gag att gca aac aaa caa aag gct acc ctc gtg     480
Glu Pro Ser Lys Ala Glu Ile Ala Asn Lys Gln Lys Ala Thr Leu Val
            130                 135                 140 tgc ttg gcc agg ggc ttc ttc cct gac cac gtg gag ctg agc tgg tgg     528
Cys Leu Ala Arg Gly Phe Phe Pro Asp His Val Glu Leu Ser Trp Trp
        145                 150                 155 gtg aat ggc aag gag gtc cac agt ggg gtc agc acg gac cct cag gcc     576
Val Asn Gly Lys Glu Val His Ser Gly Val Ser Thr Asp Pro Gln Ala
    160                 165                 170 tac aag gag agc aat tat agc tac tgc ctg agc agc cgc ctg agg gtc     624
Tyr Lys Glu Ser Asn Tyr Ser Tyr Cys Leu Ser Ser Arg Leu Arg Val
175                 180                 185                 190 tct gct acc ttc tgg cac aat cct cga aac cac ttc cgc tgc caa gtg     672
Ser Ala Thr Phe Trp His Asn Pro Arg Asn His Phe Arg Cys Gln Val
                195                 200                 205 cag ttc cat ggg ctt tca gag gag gac aag tgg cca gag ggc tca ccc     720
Gln Phe His Gly Leu Ser Glu Glu Asp Lys Trp Pro Glu Gly Ser Pro
            210                 215                 220 aaa cct gtc aca cag aac atc agt gca gag gcc tgg ggc cga gca gac     768
Lys Pro Val Thr Gln Asn Ile Ser Ala Glu Ala Trp Gly Arg Ala Asp
        225                 230                 235 tgt gga atc act tca gca tcc tat cat cag ggg gtt ctg tct gca acc     816
Cys Gly Ile Thr Ser Ala Ser Tyr His Gln Gly Val Leu Ser Ala Thr
    240                 245                 250 atc ctc tat gag atc cta ctg ggg aag gcc acc cta tat gct gtg ctg     864
Ile Leu Tyr Glu Ile Leu Leu Gly Lys Ala Thr Leu Tyr Ala Val Leu
255                 260                 265                 270 gtc agt ggc ctg gtg ctg atg gcc atg gtc aag aaa aaa aat tcc tga     912
Val Ser Gly Leu Val Leu Met Ala Met Val Lys Lys Lys Asn Ser
```

<210> SEQ ID NO 7
<211> LENGTH: 303
<212> TYPE: PRT
<213> ORGANISM: Mus musculus

<400> SEQUENCE: 7

```
Met Gly Ser Arg Leu Phe Phe Val Val Leu Ile Leu Leu Cys Ala Lys
            -15                 -10                  -5
His Met Glu Ala Ala Val Thr Gln Ser Pro Arg Ser Lys Val Ala Val
    -1   1               5                  10
Thr Gly Gly Lys Val Thr Leu Ser Cys His Gln Thr Asn Asn His Asp
 15              20                  25                  30
Tyr Met Tyr Trp Tyr Arg Gln Asp Thr Gly His Gly Leu Arg Leu Ile
             35                  40                  45
His Tyr Ser Tyr Val Ala Asp Ser Thr Glu Lys Gly Asp Ile Pro Asp
         50                  55                  60
Gly Tyr Lys Ala Ser Arg Pro Ser Gln Glu Asn Phe Ser Leu Ile Leu
             65                  70                  75
Glu Leu Ala Ser Leu Ser Gln Thr Ala Val Tyr Phe Cys Ala Ser Ser
         80                  85                  90
Glu Gly Arg Glu Ala Glu Gln Phe Phe Gly Pro Gly Thr Arg Leu Thr
 95                 100                 105                 110
Val Leu Glu Asp Leu Arg Asn Val Thr Pro Pro Lys Val Ser Leu Phe
            115                 120                 125
Glu Pro Ser Lys Ala Glu Ile Ala Asn Lys Gln Lys Ala Thr Leu Val
            130                 135                 140
Cys Leu Ala Arg Gly Phe Phe Pro Asp His Val Glu Leu Ser Trp Trp
            145                 150                 155
Val Asn Gly Lys Glu Val His Ser Gly Val Ser Thr Asp Pro Gln Ala
            160                 165                 170
Tyr Lys Glu Ser Asn Tyr Ser Tyr Cys Leu Ser Ser Arg Leu Arg Val
175                 180                 185                 190
Ser Ala Thr Phe Trp His Asn Pro Arg Asn His Phe Arg Cys Gln Val
            195                 200                 205
Gln Phe His Gly Leu Ser Glu Glu Asp Lys Trp Pro Glu Gly Ser Pro
            210                 215                 220
Lys Pro Val Thr Gln Asn Ile Ser Ala Glu Ala Trp Gly Arg Ala Asp
            225                 230                 235
Cys Gly Ile Thr Ser Ala Ser Tyr His Gln Gly Val Leu Ser Ala Thr
            240                 245                 250
Ile Leu Tyr Glu Ile Leu Leu Gly Lys Ala Thr Leu Tyr Ala Val Leu
255                 260                 265                 270
Val Ser Gly Leu Val Leu Met Ala Met Val Lys Lys Asn Ser
            275                 280                 285
```

<210> SEQ ID NO 8
<211> LENGTH: 825
<212> TYPE: DNA
<213> ORGANISM: Mus musculus
<220> FEATURE:
<221> NAME/KEY: CDS
<222> LOCATION: (1)..(822)
<221> NAME/KEY: sig_peptide
<222> LOCATION: (1)..(63)
<221> NAME/KEY: mat_peptide
<222> LOCATION: (64)..(822)

```
<400> SEQUENCE: 8 atg ctg att cta agc ctg ttg gga gca gcc ttt ggc tcc att tgt ttt      48
Met Leu Ile Leu Ser Leu Leu Gly Ala Ala Phe Gly Ser Ile Cys Phe
    -20              -15              -10 gca gca acc agc atg gcc cag aag gta aca cag act cag act tca att      96
Ala Ala Thr Ser Met Ala Gln Lys Val Thr Gln Thr Gln Thr Ser Ile
 -5              -1  1               5                    10 tct gtg gtg gag aag aca acg gtg aca atg gac tgt gtg tat gaa acc     144
Ser Val Val Glu Lys Thr Thr Val Thr Met Asp Cys Val Tyr Glu Thr
             15                  20                  25 cgg gac agt tct tac ttc tta ttc tgg tac aag caa aca gca agt ggg     192
Arg Asp Ser Ser Tyr Phe Leu Phe Trp Tyr Lys Gln Thr Ala Ser Gly
         30                  35                  40 gaa ata gtt ttc ctt att cgt cag gac tct tac aaa aag gaa aat gca     240
Glu Ile Val Phe Leu Ile Arg Gln Asp Ser Tyr Lys Lys Glu Asn Ala
     45                  50                  55 aca gtg ggt cat tat tct ctg aac ttt cag aag cca aaa agt tcc atc     288
Thr Val Gly His Tyr Ser Leu Asn Phe Gln Lys Pro Lys Ser Ser Ile
 60                  65                  70                  75 gga ctc atc atc acc gcc aca cag att gag gac tca gca gta tat ttc     336
Gly Leu Ile Ile Thr Ala Thr Gln Ile Glu Asp Ser Ala Val Tyr Phe
                 80                  85                  90 tgt gct atg aga gag gat ggg ggc agt ggc aac aag ctc atc ttt gga     384
Cys Ala Met Arg Glu Asp Gly Gly Ser Gly Asn Lys Leu Ile Phe Gly
             95                 100                 105 act ggc act ctg ctt tct gtc aag cca aac atc cag aac cca gaa cct     432
Thr Gly Thr Leu Leu Ser Val Lys Pro Asn Ile Gln Asn Pro Glu Pro
         110                 115                 120 gct gtg tac cag tta aaa gat cct cgg tct cag gac agc acc ctc tgc     480
Ala Val Tyr Gln Leu Lys Asp Pro Arg Ser Gln Asp Ser Thr Leu Cys
 125                 130                 135 ctg ttc acc gac ttt gac tcc caa atc aat gtg ccg aaa acc atg gaa     528
Leu Phe Thr Asp Phe Asp Ser Gln Ile Asn Val Pro Lys Thr Met Glu
 140                 145                 150                 155 tct gga acg ttc atc act gac aaa act gtg ctg gac atg aaa gct atg     576
Ser Gly Thr Phe Ile Thr Asp Lys Thr Val Leu Asp Met Lys Ala Met
                 160                 165                 170 gat tcc aag agc aat ggg gcc att gcc tgg agc aac cag aca agc ttc     624
Asp Ser Lys Ser Asn Gly Ala Ile Ala Trp Ser Asn Gln Thr Ser Phe
             175                 180                 185 acc tgc caa gat atc ttc aaa gag acc aac gcc acc tac ccc agt tca     672
Thr Cys Gln Asp Ile Phe Lys Glu Thr Asn Ala Thr Tyr Pro Ser Ser
         190                 195                 200 gac gtt ccc tgt gat gcc acg ttg act gag aaa agc ttt gaa aca gat     720
Asp Val Pro Cys Asp Ala Thr Leu Thr Glu Lys Ser Phe Glu Thr Asp
 205                 210                 215 atg aac cta aac ttt caa aac ctg tca gtt atg gga ctc cga atc ctc     768
Met Asn Leu Asn Phe Gln Asn Leu Ser Val Met Gly Leu Arg Ile Leu
 220                 225                 230                 235 ctg ctg aaa gta gcg gga ttt aac ctg ctc atg acg ctg agg ctg tgg     816
Leu Leu Lys Val Ala Gly Phe Asn Leu Leu Met Thr Leu Arg Leu Trp
                 240                 245                 250 tcc agt tga                                                         825
Ser Ser

<210> SEQ ID NO 9
<211> LENGTH: 274
<212> TYPE: PRT
<213> ORGANISM: Mus musculus
```

<400> SEQUENCE: 9

```
Met Leu Ile Leu Ser Leu Leu Gly Ala Ala Phe Gly Ser Ile Cys Phe
    -20                 -15                 -10
Ala Ala Thr Ser Met Ala Gln Lys Val Thr Gln Thr Gln Thr Ser Ile
 -5           -1   1              5                   10
Ser Val Val Glu Lys Thr Thr Val Thr Met Asp Cys Val Tyr Glu Thr
             15                  20                  25
Arg Asp Ser Ser Tyr Phe Leu Phe Trp Tyr Lys Gln Thr Ala Ser Gly
         30                  35                  40
Glu Ile Val Phe Leu Ile Arg Gln Asp Ser Tyr Lys Lys Glu Asn Ala
     45                  50                  55
Thr Val Gly His Tyr Ser Leu Asn Phe Gln Lys Pro Lys Ser Ser Ile
 60                  65                  70                  75
Gly Leu Ile Ile Thr Ala Thr Gln Ile Glu Asp Ser Ala Val Tyr Phe
                 80                  85                  90
Cys Ala Met Arg Glu Asp Gly Gly Ser Gly Asn Lys Leu Ile Phe Gly
             95                  100                 105
Thr Gly Thr Leu Leu Ser Val Lys Pro Asn Ile Gln Asn Pro Glu Pro
         110                 115                 120
Ala Val Tyr Gln Leu Lys Asp Pro Arg Ser Gln Asp Ser Thr Leu Cys
     125                 130                 135
Leu Phe Thr Asp Phe Asp Ser Gln Ile Asn Val Pro Lys Thr Met Glu
140                 145                 150                 155
Ser Gly Thr Phe Ile Thr Asp Lys Thr Val Leu Asp Met Lys Ala Met
             160                 165                 170
Asp Ser Lys Ser Asn Gly Ala Ile Ala Trp Ser Asn Gln Thr Ser Phe
             175                 180                 185
Thr Cys Gln Asp Ile Phe Lys Glu Thr Asn Ala Thr Tyr Pro Ser Ser
         190                 195                 200
Asp Val Pro Cys Asp Ala Thr Leu Thr Glu Lys Ser Phe Glu Thr Asp
     205                 210                 215
Met Asn Leu Asn Phe Gln Asn Leu Ser Val Met Gly Leu Arg Ile Leu
220                 225                 230                 235
Leu Leu Lys Val Ala Gly Phe Asn Leu Leu Met Thr Leu Arg Leu Trp
                 240                 245                 250
Ser Ser
```

<210> SEQ ID NO 10
<211> LENGTH: 822
<212> TYPE: DNA
<213> ORGANISM: Mus musculus
<220> FEATURE:
<221> NAME/KEY: CDS
<222> LOCATION: (1)..(819)
<221> NAME/KEY: sig_peptide
<222> LOCATION: (1)..(63)
<221> NAME/KEY: mat_peptide
<222> LOCATION: (61)..(819)

<400> SEQUENCE: 10

```
atg ctg att cta agc ctg ttg gga gca gcc ttt ggc tcc att tgt ttt    48
Met Leu Ile Leu Ser Leu Leu Gly Ala Ala Phe Gly Ser Ile Cys Phe
    -20                 -15                 -10              -5 gca acc agc atg gcc cag aag gta aca cag act cag act tca att tct    96
Ala Thr Ser Met Ala Gln Lys Val Thr Gln Thr Gln Thr Ser Ile Ser
             -1   1               5                   10
```

-continued

```
gtg atg gag aag aca acg gtg aca atg gac tgt gtg tat gaa acc cag        144
Val Met Glu Lys Thr Thr Val Thr Met Asp Cys Val Tyr Glu Thr Gln
         15                  20                  25 gac agt tct tac ttc tta ttc tgg tac aag caa aca gca agt ggg gaa        192
Asp Ser Ser Tyr Phe Leu Phe Trp Tyr Lys Gln Thr Ala Ser Gly Glu
     30                  35                  40 ata gtt ttc ctt att cgt cag gac tct tac aaa aag gaa aat gca aca        240
Ile Val Phe Leu Ile Arg Gln Asp Ser Tyr Lys Lys Glu Asn Ala Thr
 45                  50                  55                  60 gtg ggt cat tat tct ctg aac ttt cag aag cca aaa agt tcc atc gga        288
Val Gly His Tyr Ser Leu Asn Phe Gln Lys Pro Lys Ser Ser Ile Gly
                 65                  70                  75 ctc atc atc acc gcc aca cag att gag gac tca gca gta tat ttc tgt        336
Leu Ile Ile Thr Ala Thr Gln Ile Glu Asp Ser Ala Val Tyr Phe Cys
             80                  85                  90 gct atg aga gag gat ggg ggc agt ggc aac aag ctc atc ttt gga act        384
Ala Met Arg Glu Asp Gly Gly Ser Gly Asn Lys Leu Ile Phe Gly Thr
         95                  100                 105 ggc act ctg ctt tct gtc aag cca aac atc cag aac cca gaa cct gct        432
Gly Thr Leu Leu Ser Val Lys Pro Asn Ile Gln Asn Pro Glu Pro Ala
 110                 115                 120 gtg tac cag tta aaa gat cct cgg tct cag gac agc acc ctc tgc ctg        480
Val Tyr Gln Leu Lys Asp Pro Arg Ser Gln Asp Ser Thr Leu Cys Leu
125                 130                 135                 140 ttc acc gac ttt gac tcc caa atc aat gtg ccg aaa acc atg gaa tct        528
Phe Thr Asp Phe Asp Ser Gln Ile Asn Val Pro Lys Thr Met Glu Ser
                 145                 150                 155 gga acg ttc atc act gac aaa act gtg ctg gac atg aaa gct atg gat        576
Gly Thr Phe Ile Thr Asp Lys Thr Val Leu Asp Met Lys Ala Met Asp
             160                 165                 170 tcc aag agc aat ggg gcc att gcc tgg agc aac cag aca agc ttc acc        624
Ser Lys Ser Asn Gly Ala Ile Ala Trp Ser Asn Gln Thr Ser Phe Thr
         175                 180                 185 tgc caa gat atc ttc aaa gag acc aac gcc acc tac ccc agt tca gac        672
Cys Gln Asp Ile Phe Lys Glu Thr Asn Ala Thr Tyr Pro Ser Ser Asp
 190                 195                 200 gtt ccc tgt gat gcc acg ttg act gag aaa agc ttt gaa aca gat atg        720
Val Pro Cys Asp Ala Thr Leu Thr Glu Lys Ser Phe Glu Thr Asp Met
205                 210                 215                 220 aac cta aac ttt caa aac ctg tca gtt atg gga ctc cga atc ctc ctg        768
Asn Leu Asn Phe Gln Asn Leu Ser Val Met Gly Leu Arg Ile Leu Leu
                 225                 230                 235 ctg aaa gta gcc gga ttt aac ctg ctc atg acg ctg agg ctg tgg tcc        816
Leu Lys Val Ala Gly Phe Asn Leu Leu Met Thr Leu Arg Leu Trp Ser
             240                 245                 250 agt tga                                                                 822
Ser
```

<210> SEQ ID NO 11
<211> LENGTH: 273
<212> TYPE: PRT
<213> ORGANISM: Mus musculus

<400> SEQUENCE: 11

```
Met Leu Ile Leu Ser Leu Leu Gly Ala Ala Phe Gly Ser Ile Cys Phe
-20                 -15                 -10                  -5

Ala Thr Ser Met Ala Gln Lys Val Thr Gln Thr Gln Thr Ser Ile Ser
                 -1  1                   5                  10

Val Met Glu Lys Thr Thr Val Thr Met Asp Cys Val Tyr Glu Thr Gln
         15                  20                  25
```

```
Asp Ser Ser Tyr Phe Leu Phe Trp Tyr Lys Gln Thr Ala Ser Gly Glu
        30                  35                  40

Ile Val Phe Leu Ile Arg Gln Asp Ser Tyr Lys Lys Glu Asn Ala Thr
45                      50                  55                  60

Val Gly His Tyr Ser Leu Asn Phe Gln Lys Pro Lys Ser Ser Ile Gly
                65                  70                  75

Leu Ile Ile Thr Ala Thr Gln Ile Glu Asp Ser Ala Val Tyr Phe Cys
            80                  85                  90

Ala Met Arg Glu Asp Gly Gly Ser Gly Asn Lys Leu Ile Phe Gly Thr
        95                 100                 105

Gly Thr Leu Leu Ser Val Lys Pro Asn Ile Gln Asn Pro Glu Pro Ala
    110                 115                 120

Val Tyr Gln Leu Lys Asp Pro Arg Ser Gln Asp Ser Thr Leu Cys Leu
125                 130                 135                 140

Phe Thr Asp Phe Asp Ser Gln Ile Asn Val Pro Lys Thr Met Glu Ser
            145                 150                 155

Gly Thr Phe Ile Thr Asp Lys Thr Val Leu Asp Met Lys Ala Met Asp
            160                 165                 170

Ser Lys Ser Asn Gly Ala Ile Ala Trp Ser Asn Gln Thr Ser Phe Thr
        175                 180                 185

Cys Gln Asp Ile Phe Lys Glu Thr Asn Ala Thr Tyr Pro Ser Ser Asp
    190                 195                 200

Val Pro Cys Asp Ala Thr Leu Thr Glu Lys Ser Phe Glu Thr Asp Met
205                 210                 215                 220

Asn Leu Asn Phe Gln Asn Leu Ser Val Met Gly Leu Arg Ile Leu Leu
            225                 230                 235

Leu Lys Val Ala Gly Phe Asn Leu Leu Met Thr Leu Arg Leu Trp Ser
            240                 245                 250

Ser
```